(12) United States Patent
Ceballos et al.

(10) Patent No.: US 11,747,336 B1
(45) Date of Patent: Sep. 5, 2023

(54) RAPID DETECTION TESTS WITH PRELOADED DETECTION PARTICLES

(71) Applicant: xBiologix, Inc., Corvallis, OR (US)

(72) Inventors: Eduardo Ceballos, Corvallis, OR (US); Dan Danai Tanaree, Corvallis, OR (US)

(73) Assignee: xBiologix, Inc., Corvallis, OR (US)

( * ) Notice: Subject to any disclaimer, the term of this patent is extended or adjusted under 35 U.S.C. 154(b) by 0 days.

(21) Appl. No.: 17/855,612

(22) Filed: Jun. 30, 2022

(51) Int. Cl.
*A61P 31/14* (2006.01)
*C07K 16/10* (2006.01)
*G01N 33/543* (2006.01)
*G01N 33/569* (2006.01)
*G01N 33/68* (2006.01)

(52) U.S. Cl.
CPC . *G01N 33/56983* (2013.01); *G01N 33/54346* (2013.01); *G01N 33/54388* (2021.08)

(58) Field of Classification Search
CPC ... A61P 31/14; C07K 16/10; A61K 2039/505; A61K 2039/507; G01N 2333/165
See application file for complete search history.

(56) References Cited

U.S. PATENT DOCUMENTS

| 2019/0077776 A1 | 3/2019 | Mehl et al. |
| 2021/0072238 A1 | 3/2021 | Mehl et al. |

FOREIGN PATENT DOCUMENTS

| WO | 2016/176689 A1 | 11/2016 |
| WO | 2022/109075 A1 | 5/2022 |

OTHER PUBLICATIONS

Zambry et al., "Utilizing Electrochemical-Based Sensing Approaches for the Detection of SARS-CoV-2 in Clinical Samples: A Review", Biosensors, 2022, published Jun. 29, 2022).*
Wang et al., "Gold nanoparticles in virus detection: Recent advances and potential considerations for SARS-CoV-2 testing development", Nanomedicine and Nanobiotechnology, 2021:1-30.*
Tokel et al. "Advances in Plasmonic Technologies for Pointof Care Applications", 2014, American Chemical Society, 114:5728-5752.*
Khlebtsov et al., "Qunatifying the Numbers of Gold Nanoparticles in the Test Zone of Lateral Flow Immunoassay Strips," ACS Appl Nano Materials, pp. 9 (Jun. 28, 2019).

* cited by examiner

*Primary Examiner* — Barry A Chestnut
(74) *Attorney, Agent, or Firm* — Dicke, Billig & Czaja, PLLC

(57) ABSTRACT

Examples are directed to rapid detection test (RDT) devices, apparatuses, and methods of forming RDT devices and/or apparatuses that include detection particles preloaded in a test region. An example RDT apparatus includes a substrate, and a test region disposed on a first portion of the substrate. The test region including: a first set of detection particles that exhibit a first detectable label, and a set of capture agents configured to bind to a target analyte in a biological sample, each of the set of capture agents including a first ligand configured to bind to the target analyte. The RDT apparatus further includes a second set of detection particles that exhibit a second detectable label, wherein each of the second set of detection particles includes a label protein including a second ligand configured to bind to the target analyte.

20 Claims, 11 Drawing Sheets

RAPID DETECTION TESTS WITH PRELOADED DETECTION PARTICLES

BACKGROUND

Researchers are increasingly engaged in assay development and detection methods for various applications and instrumentation to detect analytes. A platform for affinity assays or detection may involve immobilizing antibodies or other proteins onto nitrocellulose surfaces. Various types of assays are used for different detection tests. A variety of biological samples may be tested using such assays, including urine, saliva, sweat, serum, plasma, whole blood and other fluids or solids suspended in a fluid. Industries in which such assays may be employed include veterinary medicine, human medicine, quality control, product safety in food production, and environmental health and safety, among others. In these areas of utilization, rapid tests are used to screen for animal diseases, pathogens, chemicals, toxins and water pollutants, among other purposes.

SUMMARY

The present invention is directed to overcoming the above-mentioned challenges and others related to test for detecting target analytes, such as those involving detection particles that exhibit a detectable label that are preloaded on the test region of the test. The test may be used to detect different target analytes, including but not limited to viruses, such as those associated with coronaviruses, bacteria, toxins, and pollutants.

Some aspects are directed to a rapid detection test (RDT) apparatus comprising a substrate and a test region disposed on a first portion of the substrate, the test region including a first set of detection particles that exhibit a first detectable label, and a set of capture agents configured to bind to a target analyte in a biological sample, each of the set of capture agents including a first ligand configured to bind to the target analyte. The RDT apparatus further comprises a second set of detection particles that exhibit a second detectable label, wherein each of the second set of detection particles includes a label protein including a second ligand configured to bind to the target analyte.

In some aspects, a first subset of the set of capture agents are bound to the substrate and a second subset of the set of capture agents form part of the first set of detection particles.

In some aspects, the first set of detection particles include a concentration of the first detectable label that provides a signal below a detection threshold associated with the first detectable label, wherein the signal is human visible or machine detectable.

In some aspects, the first ligand and the second ligand is configured to bind to a spike glycoprotein or other target of severe acute respiratory syndrome coronavirus 2 (SARs-CoV-2).

In some aspects, the first detectable label of the first set of detection particles is different from the second detectable label of the second set of detection particles. In some aspects, the first detectable label of the first set of detection particles is the same as the second detectable label of the second set of detection particles.

In some aspects, the first ligand and the second ligand are different from one another.

In some aspects, the apparatus further includes a control region disposed on a third portion of the substrate, the control region including a set of control agents, each of the control agents including an analyte protein and where the label protein includes the second ligand configured to bind to both the target analyte and the analyte protein of the set of control agents.

In some aspects, the apparatus further includes at least one of: a sample input region disposed on a second portion of the substrate, the sample input region including the second set of detection particles; and a sample container that includes a solution with the second set of detection particles, the sample container configured to receive the biological sample and to provide the biological sample and the second set of detection particles to a sample input region of the substrate.

In some aspects, the each of the first set and second set of detection particles are a gold nanoparticle (AuNP) or a latex nanoparticle respectively functionalized with one of the first ligand and the label protein.

Some aspects are directed to a rapid detection test (RDT) device comprising a substrate and a test region disposed on a first portion of the substrate, the test region including a first set of detection particles that exhibit a first detectable label, and a set of capture agents configured to bind to a target analyte in a biological sample, each of the capture agents including a first ligand configured to bind to the target analyte. And, the RDT further comprises a sample input region disposed on a second portion of the substrate, the sample input region including a second set of detection particles that exhibit a second detectable label, wherein each of the second set of detection particles includes a label protein including a second ligand configured to bind to the target analyte.

In some aspects, the first set of detection particles include a concentration of the first detectable label that provides a signal below a detection threshold associated with the first detectable label and lowers a limit of detection of the RDT device.

In some aspects, the target analyte is associated with severe acute respiratory syndrome coronavirus 2 (SARs-CoV-2), and wherein a first subset of the set of capture agents are bound to the substrate and a second subset of the set of capture agents form part of the first set of detection particles.

In some aspects, the RDT device further including a control region disposed on a third portion of the substrate, the control region including a set of control agents, each of the control agents including an analyte protein and where the label protein includes the second ligand configured to bind to both the target analyte and the analyte protein of the set of control agents.

In some aspects, each of the first set of detection particles is a gold nanoparticle (AuNP) or a latex nanoparticle, and each of the second set of detection particles is an AuNP or a latex nanoparticle functionalized with at least one of the label protein.

Some aspects are directed to a method comprising forming a test region in a first portion of a substrate by depositing a first subset of capture agents including a first ligand configured to bind to a target analyte in a biological sample, depositing a first set of detection particles that exhibit a first detectable label to the first portion of the substrate such that the test region includes a volume, and forming a second set of detection particles that exhibit a second detectable label, wherein each of the second set of detection particles includes a label protein including a second ligand configured to bind to the target analyte.

In some aspects, depositing the first set of detection particles includes depositing a concentration of the first detectable label that provide a signal below a detection threshold associated with the label protein such that the first detectable label is preloaded on the test region to a level below a detection limit of the first detectable label.

In some aspects, the method further includes determining the concentration of the first detectable label to preload onto the test region.

In some aspects, each of the first set of detection particles further include a capture agent of a second subset of the capture agents, and the method further includes preparing the first set of detection particles by binding the second subset of the capture agents to a surface of the first set of detection particles.

In some aspects, the method further includes depositing at least one blocking agent to at least one of: the test region, the first set of detection particles, and the second set of detection particles.

DETAILED DESCRIPTION

Figure 1:
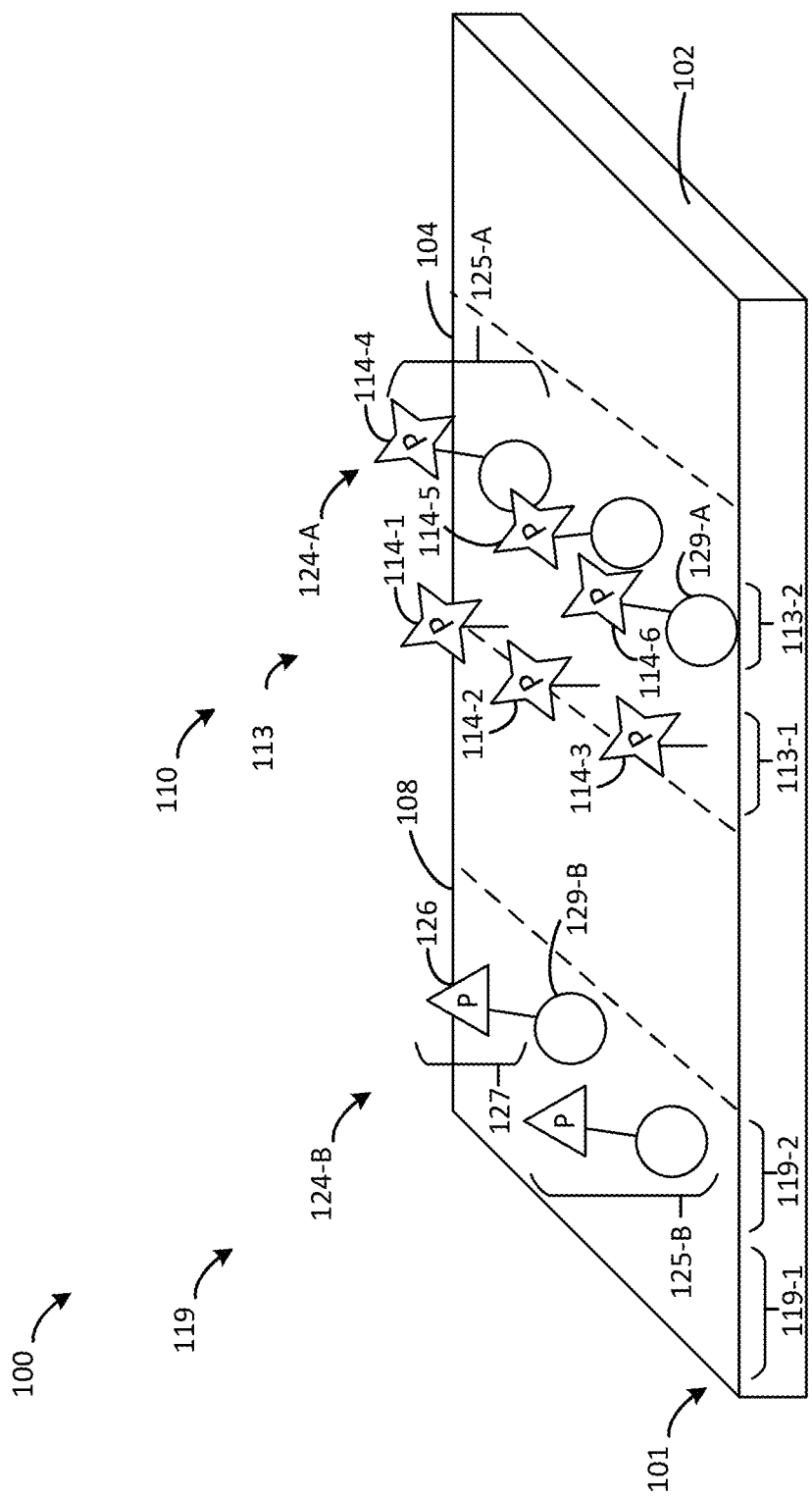
FIG. 1 is a schematic illustration of an example rapid detection test (RDT) apparatus.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

In recent years, there has been an increasing demand for point-of-care diagnostic or other detection tests to provide the rapid and simultaneous detection of a target analyte present in biological samples. To reduce costs, it may be beneficial for such detection tests to be easy to perform without the use of laboratory investigation, or individuals trained in chemical analysis. Moreover, transmission of pathogens, such as influenza, severe acute respiratory syndrome coronavirus 2 (SARS-CoV-2) and others, may persist and begin to circulate seasonally. For instance, with regards to Coronavirus Disease 2019 (COVID-19) (the disease caused by the SARS-CoV-2 virus), sustained and widespread surveillance may be needed for several years to avoid resurgence. Rapid detection tests (RDT) may use an immunological assay where detection of a target analyte depends on accumulating a threshold amount of detectable label in a test region, which is beyond a detection threshold. In many instances, the RDTs accumulate a colorant or other optically detectable label in the test region which is human visible or machine detectable when accumulated beyond the detection threshold. The detection threshold may be defined as a concentration of detectable label, e.g., a number of detectable labels per millimeter squared (label/mm$^2$), for the signal to be detected. As an example, the detection threshold may be associated with turning the test region a visible color which is detectable by a human eye.

The detection threshold is related to the limit of detection (LOD) or the load detection limit for detecting a target analyte. Typically, lateral flow assays (LFA) and other types of RDTs have orders of magnitudes higher LOD than other types of tests, such as polymerase chain reaction (PCR) tests. As the LOD is higher, the amount of target analyte (e.g., virus) needed to be detected by the LFA is higher, e.g., there is a higher load detection limit for the tests. For LFAs, at least one target analyte per detectable label is needed to be captured on the test line. Accumulating the detectable label to meet the detection threshold is a limiting factor for LOD.

Examples of the present disclosure lower the LOD, and thus lower the amount of target analyte required for detection, by preloading detectable labels in a test region of an RDT device. For example, detection particles that exhibit the detectable label are preloaded in the test region to a concentration that provides a signal below a detection limit associated with the detectable label. As the signal is below the detection limit, a human or machine may be unable to detect the signal. For example, a colorant exhibited by the detection particles may be not visible to a human eye. As further described below, the test region further includes a set of capture agents that include a first ligand that binds to a target analyte in a biological sample. Additional detection particles, that exhibit a second detectable label and include a label protein including a second ligand that binds to the target analyte, interact with the biological sample before flowing or otherwise being provided to the test region of the RDT device. In response to target analyte being present in the biological sample, at least some of the additional detection particles bind to the capture agents in the test region, causing accumulation of the second detectable label. The accumulated second detectable label may add to the signal provided by the first detectable label, and once the detection threshold is reached, the signal is detectable. For example, the presence of the target analyte may be detected, either via a visible colorant or machine detectable signal. The first and second detectable labels may be the same label or different labels which provide signals that are additive to one another. The preloaded first detectable label thereby lowers a target analyte load for crossing the detection threshold and lowers the LOD as compared to no preloading of detection labels.

Various examples are directed to an RDT apparatus, device, and/or kit, as well as method of forming the same, comprising a substrate with different regions and including detection particles that exhibit a first detectable label on a test region of the different regions. Reagents for driving the test may be deposited on the substrate, such as by digital printing and/or manually or other automated techniques, such as soaking or otherwise. The substrate may include the test region including the first set of detection particles that exhibit a first detectable label, and a set of capture agents including a first ligand that bind to a target analyte in a biological sample. The RDTs may further include a second set of detection particles, which may form part of the RDT device or may be separate therefrom and in a solution, as further described herein. The second set of detection particles exhibit a second detectable label, such as a visual color or fluorescence, and further include a label protein including a second ligand to enable the second set of detection particles to act as a label, as further described herein. The substrate may optionally include other regions, such as a control region including control agents.

As used herein, a test region refers to or includes a portion on the substrate where qualitatively assessing or quantitatively measuring the presence, amount, or functional activity of a target analyte may be performed. The capture agents refer to or include molecules or compounds which are bound (directly or indirectly) to the substrate and which are configured to bind to the target analyte. A control region refers to or includes a portion on the substrate where qualitative assessing of the functioning of the RDT may be performed. For example, the control region may be assessed to verify that the reagents function properly in the absence of the target analyte (e.g., did the test work or not). The control agents refer to or include molecules or compounds which are bound (directly or indirectly) to the substrate and which are configured to bind to the second set of detection particles. Detection particles refer to or include particles which exhibit a detectable label (e.g., signal) and, optionally, include a ligand (e.g., protein) configured to bind to at least one of the target analyte and the control agents. The RDT devices and/or apparatuses may further include a sample input region which includes or refers to a portion of the substrate configured to receive a biological sample, and in some examples, may contain the second set of detection particles. In some examples, the sample input region may include a sample sub-region to receive the biological sample and a conjugate sub-region that includes the second set of detection particles.

As used herein, a protein refers to or includes a molecule comprising chains of amino acids, and which may fold into a three dimensional structure. Proteins, such as the analyte protein, target analyte, label protein, and/or tetrazine-modified protein, are not limited to full proteins and may include functional protein fragments. As used throughout, an analyte protein may include or be referred to as an analyte functional protein fragment and a label protein may include or be referred to as a label functional protein fragment. Similarly, a tetrazine-modified protein may include or be referred to as a tetrazine-modified functional protein fragment.

As used herein, a ligand refers to or includes a molecule that binds to another molecule. A target analyte refers to or includes a molecule that binds to a ligand, and which the RDT may be designed to detect. A particle refers to or includes a material formed in a three-dimensional shape, such as a sphere, an ellipsoid, oblate spheroid, and prolate spheroid shapes. The particle may exhibit a detectable label or be functionalized to exhibit the detectable label.

As may be appreciated, many diagnostic approaches begin testing after a patient is symptomatic. As an illustration, an infectious disease may have a 3-day latent period in which a patient is infected but asymptomatic. At this point, the patient may have approximately 100 copies of a viral protein in a sample. At day 5, the patient begins exhibiting symptoms, and on day 9 the patient obtains a test. The patient may not receive the results from their testing until around day 14 (e.g., 14 days after they became infected), at which point the patient may have as many as $10^{\wedge}6$ copies of the viral protein in a sample. Throughout the entire 14 day period, the patient has been infected and capable of transmitting the infection to persons nearby. As such, testing for a pathogen after a patient begins to display symptoms does not prevent the spread of the infection. Detecting early enough to stop the spread requires testing and diagnosis before symptoms appear, such as when the LOD for the pathogen is around 100 virus copies per sample. Accordingly, a need exists for a portable assay device, that is specific for detecting a particular analyte, sensitive enough to detect small volumes of the analyte, and scalable for mass-production and use in a point-of-care setting. Although the above-describes a viral pathogen and diagnostics, examples are not so limited and may be directed to other pathogens or analytes and/or for detection purposes other than diagnostics. Other example pathogens include bacteria, fungi, protozoa, worms, and microbes, among others. Example analytes, which may or may not be a pathogen, include radioactive material or components, enzymes, toxins, pollutants, and food allergens, among others.

Figure 3:
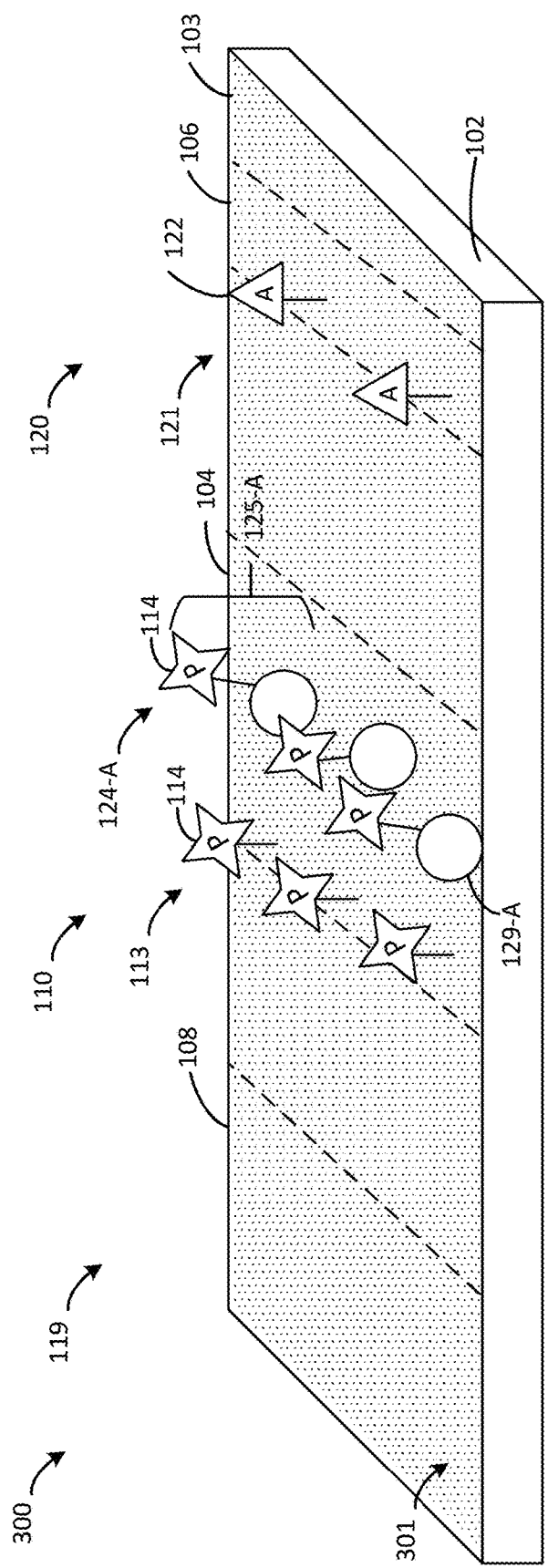
FIG. 3 is a schematic illustration of an example kit including an RDT device.
Figure 3:
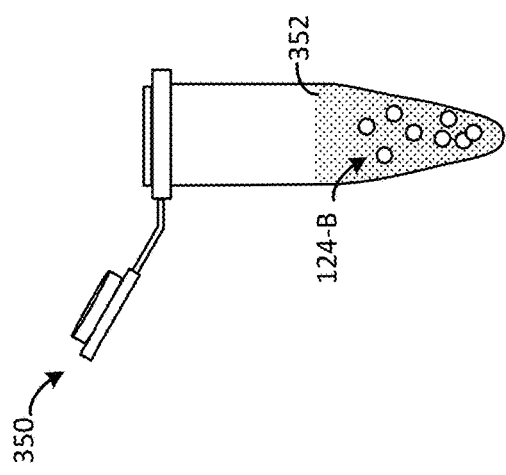

Turning now to the figures, FIG. 1 is a schematic illustration of an example RDT apparatus. The RDT apparatus 100 may include or be an RDT device 101. In some examples, the RDT apparatus 100 further includes other components, such as detection particles in solution as illustrated by FIG. 3.

The RDT device 101 includes a substrate 102 and a test region 110. As used herein, a substrate refers to or includes a solid or porous substance that receives the deposited layers of molecules. In some examples, the substrate 102 is formed of glass microfibers (GMF), a polymer (e.g., plastic), a metal, paper, or other material. In some examples, the substrate 102 is formed of or includes a membrane, such as a mesh membrane. In further examples, the substrate 102 may be formed of one or more of glass, GMF, a polymer, polypropylene, paper, metal, metal fibers, carbon nanotube fibers (CNTF), non-woven material, plasma treated material, and silicon.

The test region 110 is disposed or formed on a first portion 104 of the substrate 102. The test region 110 includes a set of capture agents 113 configured to bind to a target analyte in a biological sample. Each of the capture agents of the set of capture agents 113 include a first ligand 114-1, 114-2, 114-3 (and, optionally, 114-4, 114-5, 114-6) configured to bind to the target analyte.

The test region 110 further includes a first set of detection particles 124-A that exhibit a first detectable label. As previously described, detection particles refer to or include particles which exhibit a detectable label. The detectable label includes or refers to a property or signal which may be detected, such as a visual color, optical signal (e.g., fluorescence), electrical or magnetic property, radioactive property, among other labels which may be detected. The detection label may provide a signal, e.g., an optical signal, a visual signal, an electrical signal, a magnetic signal, an electromagnetic signal, among others. In some examples, the signal is optical, such as being optically or visibly detectable by a human or a machine.

The first set of detection particles 124-A may include a concentration of the first detection label that provides a signal below a detection threshold associated with the first detectable signal. The detection threshold may be associated with a human eye or a machine. For example, when the signal is above the detection threshold, the signal is human visible or machine detectable. When the signal is below the detection threshold, the signal may not be detectable, visually, optically or otherwise, by a human or machine. The first set of detection particles 124-A may be preloaded on the test region 110 to lower a LOD and/or a target load detection limit of the RDT apparatus 100 for the target analyte as compared to a test region without the first set of detection particles. In such examples, the set of detection particles 124-A may cause a step-up or decrease in the load detection limit (e.g., a lower amount of target load required to provide a signal that is detectable by a human or machine).

In some examples, the set of capture agents 113 includes a first subset 113-1 of the set of capture agents 113 bound to the substrate 102 and a second subset 113-2 of the set of capture agents 113 form part of the first set of detection particles 124-A. For example, each of the first set of detection particles 124-A may include a capture agent of the set of capture agents 113, and with each of the capture agents includes a first ligand 114-1, 114-2, 114-3, 114-4, 114-5, 114-6 (herein generally referred to as 114). In such examples, the first set of detection particles 124-A may both (i) provide the signal that is below the detection threshold of the first detectable label (e.g., provides a level of signal below the detection threshold) and (ii) actively participate in the capture of the target analyte (e.g., captures the target analyte which may or may not be bound to one of the second set of detection particles 124-B). By having capture agents on the first set of detection particles 124-A, which may bind to the target analyte, the surface area of the test region 110 which may capture a target analyte is increased, which may raise the signal and/or increase the probability of capturing the target analyte and accumulating the second detectable label with the first detectable label to provide the signal that is detectable.

The apparatus 100 further includes a second set of detection particles 124-B that exhibit a second detectable label. Each of the second set of detection particles includes a label protein 127 including a second ligand 126 configured to bind to the target analyte.

The first detectable label and the second detectable label are additive to one another. That is, a signal provided by or associated with the first detectable label may add with or to the signal provided by or associated with second detectable label. In some examples, the first detectable label may be the same as the second detectable label, such as the same colorant or fluorescent. In other examples, the first and second detectable labels are different but overlap, such as including overlapping wavelength ranges (e.g., optical, electrical, and/or magnetic). The respective particles (129-A, 129-B) may exhibit the detectable labels or otherwise be functionalized to exhibit the detectable labels.

The particles, e.g., 129-A, 129-B, forming the first detection particles and the second detection particles of the first set and second set 124-A, 124B may be the same or different. For example, the first set of detection particles 124-A may include same sized particles as the second set of detection particles 124-B. In other examples, the first set of detection particles 124-A may include different sized particles than the second set of detection particles 124-B.

In some examples, the first and second ligands 114, 126 may include the same ligands. In some examples, the first and second ligands 114, 126 are different from one another.

In some examples, and as shown by FIG. 1, the substrate 102 further includes a sample input region 119. The sample input region 119 may be disposed on a second portion 108 of the substrate 102.

In some examples, the sample input region 119 includes the second set of detection particles 124-B. For example, the second set of detection particles 124-B may be disposed on the sample input region 119 configured to receive the biological sample, wherein the test region 110 (and control region 120 as further shown by FIG. 2) are downstream from the sample input region 119 of the substrate 102. The second set of detection particles 124-B may be deposited via digital printing or other methodologies, as further described herein. In such examples, the set of detection particles 124-B form part of the RDT device 101. As such, various examples are directed to an RDT device 101 that include the substrate 102, the test region 110 including the set of capture agents 113 and the first set of detection particles 124-A, and the sample input region 119 including the second set of detection particles 124-B.

In some examples, the sample input region 119 may include two sub-regions 119-1, 119-2 juxtaposed together to form the sample input region 119. The two sub-regions 119-1, 119-2 include a sample sub-region 119-1 to receive the biological sample and a conjugate sub-region 119-2 that includes the second set of detection particles 124-B. The two sub-regions 119-1, 119-2 of the sample input region 119 are formed of the same material (e.g., the substrate 102) with the conjugate sub-region 119-2 being further treated with the second set of detection particles 124-B. The conjugate sub-region 119-2 may be downstream of the sample sub-region 119-1 or may be upstream of the sample sub-region 119-1 (not illustrated by FIG. 1). In some examples, the sample sub-region 119-1 may be overlapping, e.g., all or portions thereof, with the conjugate sub-region 119-2 or may be on top of the conjugate sub-region 119-2.

In other examples, the second set of detection particles 124-B may be initially separate from the RDT device 101, and may form part of a kit that includes the RDT device 101, as further illustrated by FIG. 3. For example, the apparatus 100 may further include a sample container that includes a solution with the second set of detection particles 124-B. The sample container may be configured to receive the biological sample and to provide or expose the biological sample and the second set of detection particles 124-B to the sample input region 119 of the substrate 102.

In some examples, each of the first set of detection particles 124-A and the second set of detection particles 124-B is a gold nanoparticle (AuNP) functionalized with at least one of the first ligand 114 and the second ligand 126. In other examples, each of the first and second sets of detection particles 124-A, 124-B is a latex nanoparticle functionalized with at least one of the first ligands 114 and second ligands 126. In some examples, the latex nanoparticles include a colored, fluorescent, magnetic, radioactive, and/or paramagnetic latex particle. However, examples are not so limited and the particles (e.g., 129-A, 129-B), such as nanoparticles functionalized with first ligands 114 and second ligands 126, may be formed of other material, such as glass, polymer, silica, alumina, silicon carbide, tungsten carbide iron oxide steel, silica coated metal, boron nitride, or other suitable material. Each of the detection particles may between 1 nanometer (nm) to 10 micron (p), 1 nm and 1μ, 1 nm to 500 nm, or 1 nm to 100 nm in diameter as non-limiting examples. In some examples, the first set of detection particles 124-A may not be functionalized with the first ligand 114.

The apparatus 100 and/or RDT device 101 illustrated by FIG. 1 and various figures herein may be used to implement different types of RDTs. In some examples, the RDTs include a flow test, such as a lateral flow test or a dipstick test. Examples are not limited to flow test and may include other types of RDTs.

In various examples, the apparatus 100 and/or RDT device 101 may be designed to detect the presence of a particular target analyte. For example, the first ligands 114 and the second ligands 126 may include a protein or other receptor molecule that may bind to the target analyte. As previously described, a ligand includes a molecule that binds to a target analyte or other target. An analyte includes the molecule that is being detected and/or measured, such as protein of a virus, compound, and/or other pathogens.

A variety of different target analytes may be detected using example RDTs as described herein. In some examples, the target analyte may be a pathogen, such as a virus, bacteria, or other microorganism that may cause disease in humans or in other organisms, such as other animals and/or plants, among other organisms. Example pathogens include, but are not limited to, viruses and bacteria, such as coronaviruses (e.g., COVID-19), Ebola, dengue, human immunodeficiency virus (HIV), Hantavirus, Lyme disease, Japanese encephalitis, Lassa fever, rabies, Middle Eastern Respiratory Syndrome (MERS), SARS, rotavirus, Hepatitis B, Hepatitis C, yellow fever, Rift Valley fever, Crimean-Congo hemorrhagic fever and other Arenaviruses, Clostridioides *difficile, Candida* auris, Carbapenem-resistant *Acinetobacter*, Carbapenem-resistant Enterobacteriaceae, Drug-resistant *Neisseria gonorrhoeae*, Drug-resistant Camplyobacter, Drug-resistant *Candida*, ESBL-producing Enterobacteriaceae, Vancomycin-resistant Enterococci (VRE), Drug-resistant nontyphoidal *Salmonella*, Drug-resistant *Salmonella* serotype *Typhi*, Drug-resistant *Shigella*, Methicillin-resistant *Staphylococcus aureus* (MRSA), Drug-resistant *Streptococcus pneumoniae*, Drug-resistant Tuberculosis, Erythromycin-resistant Group A *Streptococcus*, Clindamycin-resistant Group B *Streptococcus*, Azole-resistant *Aspergillus fumigatus*, Drug-resistant *Mycoplasma genitalium*, Drug-resistant *Bordetella pertussis*. For more general and specific information on example super bugs, reference is made to https://www.cdc.gov/drugresistance/biggest-threats.html, which is incorporated herein by reference in its entirety.

In some specific examples, the RDT apparatus 100 of FIG. 1 may be designed to detect a SARs infection, such a detecting the presence of COVID-19, sometimes referred to as SARs-CoV-2. For example, the first ligand 114 and second ligand 126 may be configured to bind to a spike glycoprotein or other target of SARs-CoV-2, such as a nucleocapsid glycoprotein, or an envelope glycoprotein. However, examples are not so limited and may include detecting other viruses include SARs-CoV-1, influenza, HIV, among other viruses, such as those listed above.

Additionally, examples are not limited to detecting viruses and/or for diagnosis purposes. As an example, the RDT apparatus 100 may be used to detect bacteria. Bacteria may cause disease by secreting or excreting toxins (e.g., such with botulism), by producing toxin internally, which are released when the bacteria disintegrates (e.g., such as with typhoid), or by inducing sensitivity to antigenic properties (e.g., such as in tuberculosis). Example diseases caused by bacteria include cholera, diphtheria, bacterial meningitis, tetanus, Lyme disease, gonorrhea, and syphilis. As other examples, various content, such as water and food product, may be contaminated by toxins or pathogens. As an example, water may be contaminated by disease-causing microbes or other pathogens. Waterborne pathogens may be further acquired by consuming contaminated food or beverage, from contact in the environment, or by direct contact with another organism (e.g., organism-to-organism spread). Example illnesses include Cryptosporidiosis, Cyclosporiasis. *Escherichia coli* and Hemolytic Uremic Syndrome, Giardiasis, Harmful Algal Blooms, Hot Tub Rash (*Pseudomonas* Dermatitis/Folliculitis), Legionellosis, *Naegleria fowleri* and Primary Amebic Meningoencephalitis, Norovirus Infection, Shigellosis, Swimmer's Ear (Otitis Externa), Swimmer's Itch (Cercarial Dermatitis).

The apparatus 100 illustrated by FIG. 1 may include variations. Example variations include, but are not limited to, the substrate at least partially being functionalized with a coupling agent, a control region on the RDT device that includes control agents, use of linker groups to couple different reagents to the coupling agent, use of tetrazine-modified proteins for at least one of the first ligand, and control agents, use of blocking agents applied to at least one of the test region, the control region, the sample input region, the first set of detection particles, and the second set of detection particles, among other variations. At least some of the variations are further illustrated by FIGS. 2-5J.

Figure 2:
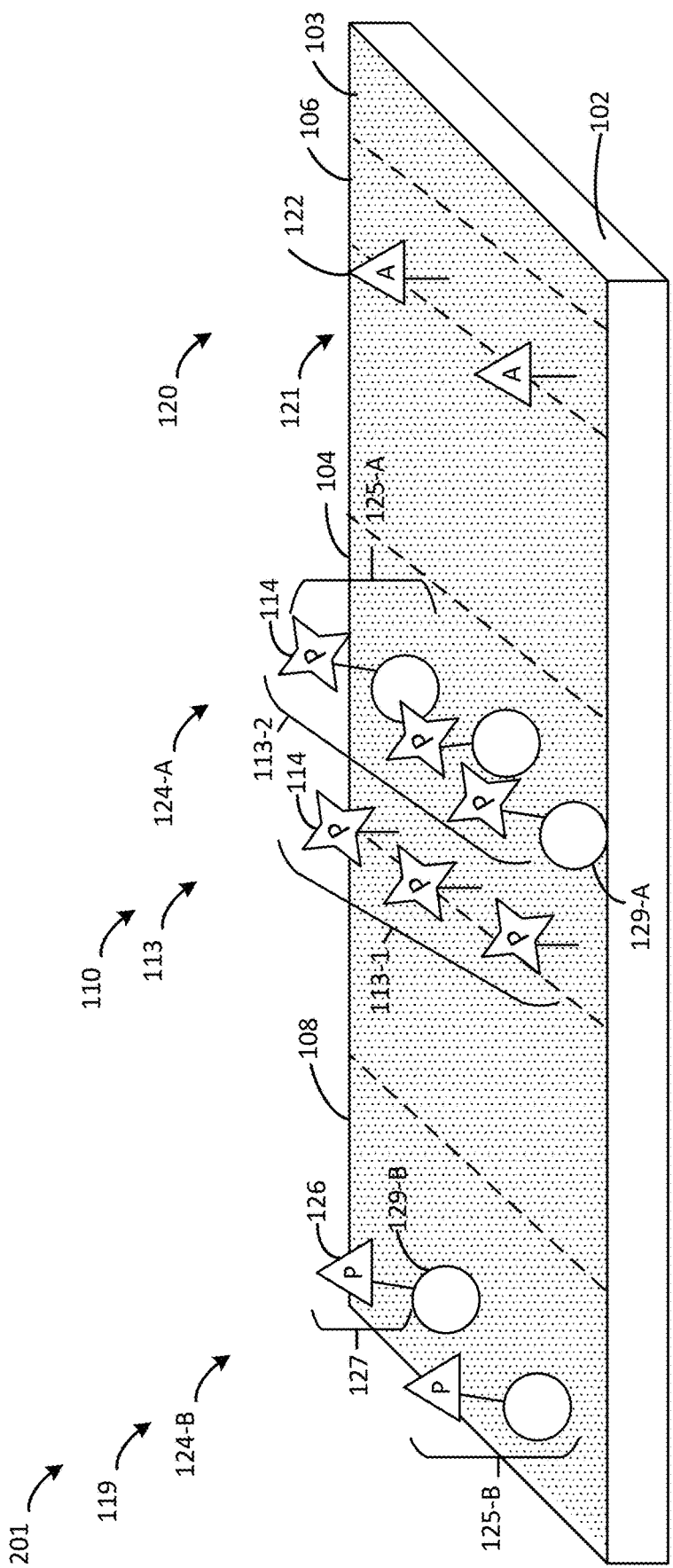
FIG. 2 is a schematic illustration of an example RDT device.

FIG. 2 is a schematic illustration of an example RDT device. Various features and attributes of the RDT device 201 of FIG. 2 may include at least substantially the same features and attributes of the RDT device 101 of FIG. 1, as shown by the common numbering and with the details of the common features and attributes not being repeated. In some examples, the RDT device 201 of FIG. 2 includes an example implementation of the RDT device 101 of FIG. 1.

As shown, the RDT device 201 include a substrate 102, a test region 110 disposed on a first portion 104 of the substrate 102, and a sample input region 119 disposed on a second portion 108 of the substrate 102. As previously described, the test region 110 includes a first set of detection particles 124-A that exhibit a first detectable label and a set of capture agents 113 configured to bind to a target analyte in a biological sample. Each of the capture agents include a first ligand 114 configured to bind to the target analyte.

In some examples, the sample input region 119 includes the second set of detection particles 124-B that exhibit a second detectable label, each of the second set of detection particles 124-B including a label protein 127 including a second ligand 126 configured to bind to the target analyte. In such examples, the second set of detection particles 124-B form part of the RDT device 201 which includes the substrate 102, the test region 110, the sample input region 119, and, optionally, the control region 120.

In other examples, the second set of detection particles 124-B are separate from the RDT device 201. For example, an apparatus may include a sample container that includes a solution with the set of detection particles 124-B, as illustrated by FIG. 3. In such examples, the apparatus may include or form part of a kit that includes the RDT device 201 and the sample container.

Further, in the example illustrated by FIG. 2, the set of capture agents 113 includes a first subset 113-1 of the set of capture agents 113 bound to the substrate 102 and a second subset 113-2 of the set of capture agents 113 form part of the first set of detection particles 124-A. As such, the first set of detection particles 124-A each include a first ligand 114.

In some examples, each of the first set of detection particles 124-A is a AuNP or a latex nanoparticle functionalized with at least one capture agent of the second subset 113-2 of the set of capture agents 113, and each of the second set of detection particles 124-B is an AuNP or a latex nanoparticle functionalized with at least one of the label protein 127. However, examples are not so limited, and the first set of detection particles 124-A and/or second set of detection particles 124-B may be formed of other material. In some examples, the first set of detection particles 124-A may not be functionalized with the second subset 113-2 of the set of capture agents 113.

As shown by FIG. 2, in some examples, the RDT device 201 (and/or the RDT apparatus 100 of FIG. 1) further includes a control region 120. The control region 120 is disposed on a third portion 106 of the substrate 102 and includes a set of control agents 121. Each of the control agents 121 include an analyte protein 122. In such examples, the label protein 127 associated with the second set of detection particles 124-B includes the second ligand 126 configured to bind to both the target analyte and the analyte protein 122 of the set of control agents 121.

In some examples, the RDT device 101 of FIG. 1 and/or the RDT device 201 of FIG. 2 may be formed of a single substrate and/or may functionalized with a coupling agent having functional groups (e.g., reactive moieties) to allow for forming the different regions (e.g., test, control, sample input, others) on the substrate. The different reagents for driving the test, including the coupling agent, may be deposited on the substrate, such as by digital printing and/or manually or other automated techniques, such as soaking or otherwise. The coupling agent may allow for the capture agents of a test region, the detection particles of the test region and/or sample input region, and/or control agents of a control region to bind to the substrate when deposited. Use of a single substrate may reduce time and expense for manufacturing the RDT devices as compared to fabricating different substrates for the test line and the control line, a sample input and conjugated pad, among other portions, and which are assembled together onto an assembly with backing and packaged. By reducing the time and expense for manufacturing, RDT device may be more quickly and widely available in response to emerging pathogens.

Referring back to FIG. 2, for example, the substrate 102 is at least partially coated with a coupling agent 103. In some examples, the entire substrate 102 is coated or covered with the coupling agent 103.

The coupling agent 103 may be deposited to at least a portion of the substrate 102. For example, the coupling agent 103 may be deposited to at least the first portion 104 and the second portion 108 of the substrate 102. In some examples, the coupling agent 103 is further deposited to the third portion 106 or to all of the top surface of the substrate 102 or the entire substrate 102. As used herein, a coupling agent refers to or includes a molecule or compound that may be used to provide a chemical bond between two materials, such as two dissimilar materials like glass and an organic molecule or compound (e.g., substrate 102 and capture agents 113-1). For example, the coupling agent 103 may be modified to include the functional group, e.g., moieties that are added to the compound. The coupling agent 103 has functional groups to which other molecules or compounds, e.g., the capture agents 113-1, detection particles 124-A, 124-B, and/or control agents 121, may bind to. In some examples, the coupling agent 103 comprises a compound or molecule functionalized (bound to a functional group selected from) with at least one of an epoxide functional group, a carboxylate functional group, an anhydride functional group, and an amine functional group, among other functional groups.

In some examples, the coupling agent 103 may be silane. For example, the coupling agent 103 comprises a silane coupling agent which may be functionalized with at least one of an epoxide functional group, a carboxylate functional group, an anhydride functional group, and an amine functional group. However examples are not so limited and may include other functional groups.

The coupling agent 103 may allow for other molecules or compounds to bind to the substrate 102 by binding to the functional groups of the coupling agent 103, which may otherwise not be capable of binding to the substrate 102 or bind at below a threshold rate. For example, the coupling agent 103 may create more surface area for a linker or other molecule or compound to bind to. In some examples, the modification or functionalization process, e.g., silanization process, may include using trimethoxysilane with NaOH pre-treatment, as further described herein. In some examples, for GMF or microfiber substrates, an epoxide, an amine, a carboxylic acid, and/or an anhydride functional silane may be used. In addition, some portions of the substrate 102 may be selectively treated with other coupling agents to afford surfaces with less tendency for non-specific binding.

Although not illustrated by FIG. 2, as further illustrated by FIG. 4, FIGS. 5A-5C, and FIG. 5G-5E, at least some of the reagents of the RDT device 201 may be attached to the substrate 102 and/or to particles (e.g., 129-A, 129-B) via the use of linkers. A linker refers to or includes a molecule that binds to the coupling agent 103 on the substrate 102 and/or binds to the particles, and is bound to the label proteins or capture agents. A linker may help differentiate what site the protein is immobilized to the substrate 102 with a corresponding reactive moiety contained in the protein. Controlling the site where a protein is immobilized to the substrate 102 is important for maintaining avidity and orientation of the protein.

Example linkers include trans-cyclooctene (TCO) including a TCO derivative, e.g., sTCO, with functional groups (e.g., moieties), for example, a TCO with an amine moiety, a TCO with a carboxylic acid moiety, a norbornene anhydride, a norbornene with an amine moiety, and/or a norbornene with a carboxylic acid moiety, among other molecules.

For example, each of the first subset 113-1 of the set of capture agents 113 may further include a first linker bound to the functional group of the coupling agent 103 in the first portion 104 of the substrate 102, wherein each of the first ligand 114 of the first subset 113-1 of the set of capture agents 113 is bound to the first linker. In some examples, each of the first set of detection particles 124-A further include a second linker bound to the particles (e.g., such as a functional group on the particle 129-A), wherein each of the first ligand 114 of the second subset 113-2 of the set of capture agents 113 is bound to the second linker. In some examples, each of the control agents 121 further include a third linker bound to the functional groups in the third portion 106 of the substrate 102, wherein the analyte protein 122 is bound to the third linker. In some examples, each of the second set of detection particles 124-B further include a fourth linker bound to the detection particles 124-B, wherein the label protein 127 is bound to the fourth linker. However examples are not so limited and the control agents 121 may not include linkers in some examples. For example, the second set of detection particle 124-B may not be bound to the substrate 102, but placed on top. Various examples include different combinations of the above, such as all reagents including linkers or different subsets including linkers.

In some examples, a blocking agent may be deposited to or on at least one of the test region 110, the control region 120, the sample input region 119, the first set of detection particles 124-A, and the second set of detection particles 124-B. As used herein, a blocking agent refers to or includes a molecule or compound that blocks (e.g., prevents, mitigates, or slows down) non-specific binding in the test region 110, in the control region 120, and/or in the first or second set of detection particles 124-A, 124-B, and/or that aids in the release of the second set of detection particles 124-B when deposited in the sample input region 119. Non-limiting example blocking agents include casein, bovine serum albumin (BSA), 5×Detector™, polyethylene glycol, and non-ionic surfactants, among other blocking agents. In some examples, the blocking agents may include compounds that react with the coupling agent 103 on the substrate 102 and modify the surface or react with the linker(s) to be less prone to non-specific binding by itself or when used in combination with another (e.g., traditional) blocking agent, for the whole substrate 102 or selected regions, e.g., the conjugate sub-region of the sample input region 119. For example, the blocking agent(s) may be used across the entire substrate 102, in particular regions, on at least some or all of the detection particles, and/or not at all. In some examples, the blocking agent(s) may react with the functional group of the substrate 102, the linker(s), and/or is non-reactive.

In some examples, the RDT device 201 (and/or RDT device 101) may include components for providing flow control. The flow rate of the analyte may be modulated to enhance the detection signal from the second detectable label of the second set of detection particles 124-B while minimizing overall test time. Some examples include temporary (physical) barriers placed in the path of the analyte flow, e.g., sugar, or putting a barrier in combination with modulating viscosity of the biological fluid including the sample, e.g., polyethylene glycol (PEG), methylcellulose, or modulate the path of the flow by way of modifying the hydrophobicity of certain regions on the substrate, such as applying polycaprolactone (PCL), or a combination thereof.

FIG. 3 is a schematic illustration of an example kit including an RDT device. As shown, the kit 300 may include an RDT device 301, which may include at least some of substantially the same features and attributes as the RDT device 101 of FIG. 1 and/or RDT device 201 of FIG. 2, as shown by the common numbering and with the common features and attributes not being repeated for ease of reference.

The kit 300 further include a sample container 350. The sample container 350 includes (e.g., stores) a solution 352 that includes the second set of detection particles 124-B in fluid. In some examples, the sample container 350 is configured to receive the biological sample and to provide the biological sample and the second set of detection particles 124-B to a sample input region 119 of the substrate 102.

Various examples include the use of tetrazine-modified proteins in at least one portion of the RDT device, which may allow for deterministic loading. Tetrazine-modified protein may be covalently bonded to a functionalized substrate and largely maintain its avidity.

The tetrazine-modified protein may be tethered to a substrate surface via a linker, as further described herein. More particularly, the tetrazine may be incorporated into a protein to enable covalent bonding of the protein to the substrate of the RDT in controlled concentration, orientation, length, and surface geometries. In some examples, the tetrazine may be incorporated to the protein to covalently bound to a particle to form a detectable particle. A substrate functionalized with a coupling agent may further enable covalent bonding of the tetrazine-modified protein to the substrate and multiple functions integrated into a single substrate. Furthermore, use of a tetrazine-modified protein may allow for deterministic loading of the reagents, which are dispense agnostic.

As used herein, "orthogonal" or "bioorthogonal" refers to or includes a molecule (e.g., an orthogonal tRNA (O-tRNA) and/or an orthogonal aminoacyl tRNA synthetase (O—RS)) that functions with endogenous components of a cell with reduced efficiency as compared to a corresponding molecule that is endogenous to the cell or translation system, or that fails to function with endogenous components of the cell.

In some examples, a substrate of an RDT device or apparatus may include a particular concentration of tethered (e.g., linked) tetrazine-modified protein that promotes a high rate of analyte binding without inhibition from neighboring ligands. The concentration of tetrazine-modified protein on the substrate may be selected as a function of the analyte to be detected, and therefore, is specific for the test to be performed.

In various examples, a substrate may be formed, which includes a bioorthogonal tethered protein in at least one portion of the substrate (e.g., test region and/or control region). The bioorthogonal tethered protein may be formed on a substrate by attaching a tetrazine-modified protein to a linker. As used herein, a bioorthogonal tethered protein refers to or includes a tetrazine-modified protein that has been attached to a linker. Also as used herein, a tetrazine-modified protein refers to or includes a protein or functional protein fragment that contains a tetrazine. The bioorthogonal tethered protein may include a ligand configured to bind to a target analyte. A concentration, a length, and an orientation of the bioorthogonal tethered protein may be configurable on the substrate.

Figure 4:
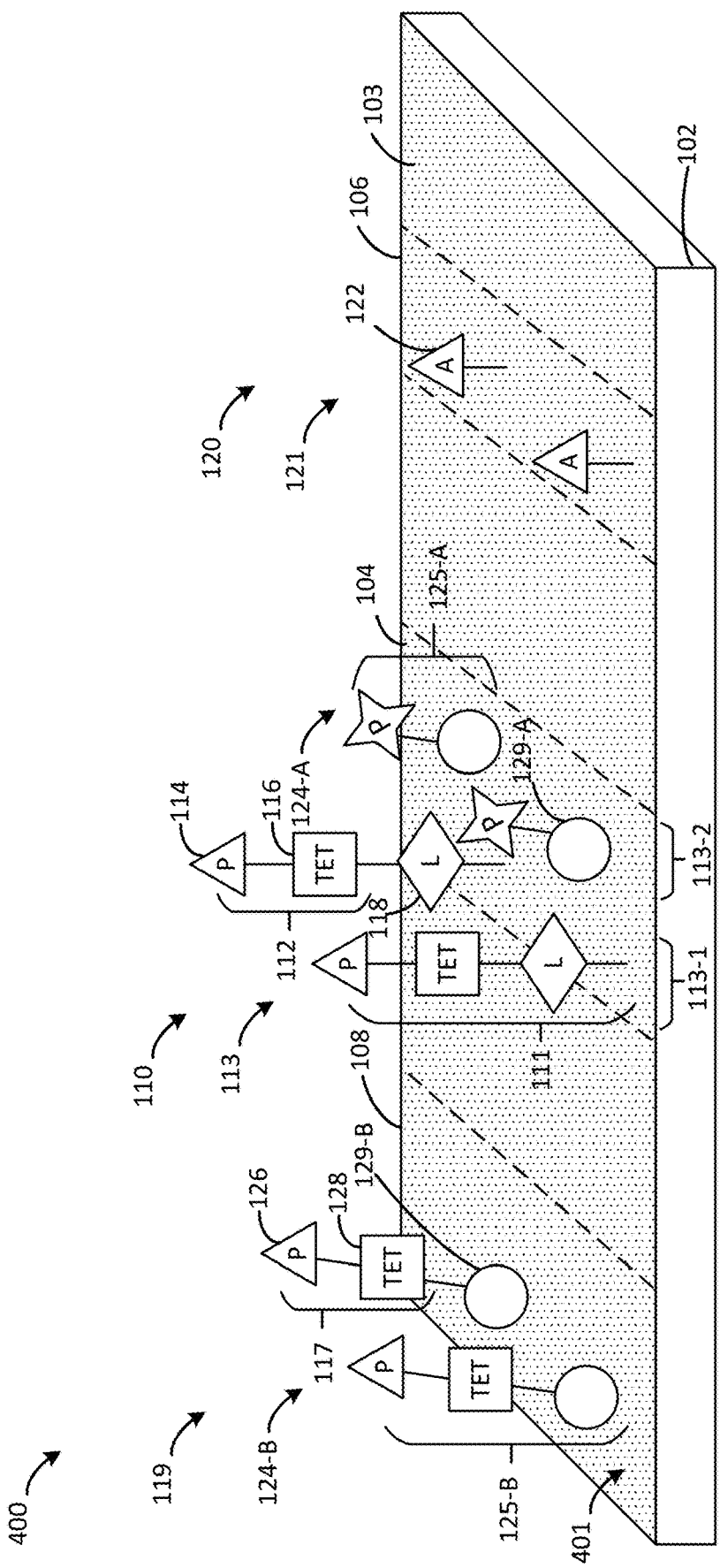
FIG. 4 is a schematic illustration of another example RDT apparatus.

FIG. 4 is a schematic illustration of another example RDT apparatus. Various features and attributes of the RDT apparatus 400 of FIG. 4 may include at least substantially the same features and attributes of the RDT apparatus 100 of FIG. 1, as shown by the common numbering and with the details of the common features and attributes not being repeated. In some examples, the RDT apparatus 400 includes an example implementation of the RDT apparatus 100 of FIG. 1, with the addition of one or more tetrazine-modified proteins as capture agents, control agents, and/or label proteins.

Similar to FIG. 1, the apparatus 400 may include or be an RDT device 401, and in some examples, may further include other components, such as detection particles in solution as illustrated by FIG. 3. The RDT device 401 includes a substrate 102, a test region 110, and, optionally, a control region 120. The substrate 102 may be at least partially coated with a coupling agent 103. In some examples, the entire substrate 102 is coated or covered with the coupling agent 103. The coupling agent 103, as previously described, includes functional groups to which other molecules or compounds, at least some of the capture agents 113 (e.g., the first subset 113-1), control agents 121, and/or detection particles may bind to.

For example, the test region 110 includes a set of capture agents 113 configured to bind to a target analyte in a biological sample. In some examples, a first subset 113-1 of the set of capture agents 113 include first bioorthogonal tethered proteins 111 including a first tetrazine-modified protein 112 and a first linker 118. The first linker may be covalently bound to the tetrazine-modified protein 112 and to functional groups of or associated with the coupling agent 103 disposed in the test region 110. The first tetrazine-modified protein 112 includes a first ligand 114 configured to bind to the target analyte. More particularly, as shown, the first tetrazine-modified protein 112 includes a tetrazine 116 bound to the first ligand 114. The test region 110 further includes the first set of detection particles 124-A, which in some examples, includes a second subset 113-2 of the set of capture agents 113. The second subset 113-2 of set of capture agents 113 may include the first ligand 114 or, although not illustrates, may include bioorthogonal tethered proteins. For example, the second subset 113-2 of capture agents 113 may include second bioorthogonal tethered proteins including a second tetrazine-modified protein and a second linker. The first and second bioorthogonal tethered proteins, including the first and second tetrazine-modified protein and first and second linkers, may be the same or different.

Further details of bioorthogonal tethered proteins is provided below, at least in connection with FIGS. 5A-5C. As used herein, the phrase "tethered" refers to or includes attaching a protein to another protein or surface by a number of bond modalities. Although FIG. 4 illustrates use of bioorthogonal tethered proteins as the capture agents, examples are not so limited. In some example, other types of proteins may be used, which bind directly or indirectly to a substrate 102 or to the coupling agent 103 in the test region 110.

In some examples and as noted above, the first tetrazine-modified protein 112 covalently binds to the first linker 118, which may maintain avidity of the protein (e.g., first ligand 114), sometimes referred to as the "orthogonality". In some examples, multimers of the first tetrazine-modified protein 112 may be prepared with one or more tetrazine moieties at a pre-selected location on the protein to control the length and orientation of the protein when immobilized on a substrate 102 (or the surface of a detection particle as further described herein). Specificity of the covalent bonding and the speed of reaction also allows for the control of loading at predetermined concentration and controlled (partial) loading on substrate (e.g., substrate 102 or detection particles 124-A). The first ligand 114 (and/or second ligand 126 and analyte protein 122) may be a variety of different types of proteins and protein fragments, and are not limited to immunoglobulin G (IgG) or IgM. For example, a functional fragment of a protein may be used. As another example, nanobodies may be used. Use of proteins that are different from IgG may allow for faster manufacturing. In some examples, the first ligand 114 (and/or second ligand 126 and analyte protein 122) may be made in cultures other than mammalian cells, such as E. coli cells, which may be faster (e.g., 3 times faster than mammalian cells) and less expensive (e.g., 1000 times less expensive than mammalian cells).

The control region 120 is disposed or formed on a third portion 106 of the substrate 102, with the second portion 108 of the substrate 102 including the sample input region 119. The control region 120 includes a set of control agents 121, each of the control agents including an analyte protein 122. In some examples, the analyte protein 122 may be bound directly or indirectly (via a linker) to the coupling agent 103 present in the third portion 106 of the substrate 102. For example, the analyte protein 122 may include a reactive moiety that may react with the functional groups of or associated with the coupling agent 103 on the substrate 102. In other examples, as shown by FIG. 5D, the analyte protein 122 may be bound indirectly to the coupling agent 103 via a third linker bound to the coupling agent 103. The analyte protein 122 refers to or includes a protein configured to bind to a detection particle (e.g., via a label protein) and is bound to the substrate 102 in the control region 120. As used herein, the analyte protein 122 may be interchangeably referred to as "a control protein" and is not the target analyte that is contained in the biological sample but may be a protein that is the same or similar to the target analyte. In some examples, the analyte protein 122 includes a second or third bioorthogonal tethered protein. In other examples, the analyte protein 122 may not include a bioorthogonal tethered protein as the control region 120 may not require optimization for low detection limit. Similarly, protein fragments or proteins other than IgG and some that are smaller than IgG may be used as the analyte protein 122.

As with FIG. 1, the apparatus 400 further includes a second set of detection particles 124-B that exhibit a second detectable label. The second set of detection particles 124-B include a label protein 127 that includes a second ligand 126 configured to bind to at least one of the target analyte and a respective control agent of the set of control agents 121.

In various examples, each detection particle 125-B of the second set of detection particles 124-B may include a second (or third) tetrazine-modified protein 117 including the second ligand 126. That is, the label proteins 127 of FIG. 1 may include a tetrazine-modified protein 117. Similar to the first tetrazine-modified protein 112, the second tetrazine-modified protein 117 includes a tetrazine 128 bound (e.g., via a carbon link) to the second ligand 126. For example, each detection particle 125-B of the second set of detection particles 124-B include a particle 129-B (e.g., bead) with the second tetrazine-modified protein 117 bound thereto. Although not illustrated by FIG. 4, each detection particle 125-B of the second set of detection particles 124-B may further include a (fourth) linker bound between the second tetrazine-modified protein 117 and the particle 129-B.

The first linkers and/or second linkers associated with the first subset 113-1 of the set of capture agents 113 and/or the first set of detection particle 124-A, and optional third linkers associated with the set of control agents 121 and/or fourth linkers associated with the set of detection particles 124 may include a same type of linker or different types of linkers, and combinations thereof. For example, each of the first, second, third, and/or fourth linkers may be selected from TCO, a TCO derivative, a TCO with an amine moiety, a TCO with a carboxylic acid moiety, a norbornene anhydride, a norbornene with an amine moiety, and a norbornene with a carboxylic acid moiety.

As previously described, linker(s) may or may not be present in the test region 110 and/or the control region 120, and/or on the first and/or second sets of detection particles 124-A, 124-B depending on the functional group(s) on the protein (e.g., first ligand 114 and analyte protein 122) that is immobilized to the substrate 102 and/or the particle 129-A, 129-B. In the case of tetrazine-modified protein, a linker may be used. In some examples, a linker may not be used if the protein contains a reactive moiety that reacts with the functional groups of the coupling agent 103 on the substrate 102 faster than those inherent to the amino acids in the protein. In some examples, if not striving for the utmost detection limit, where the site(s) on the protein immobilized to the substrate 102 is not as important, a linker may not be used.

In some examples, each of the first set of detection particles 124-A and/or the second set of detection particles 124-B is an AuNP functionalized with at least one of the first tetrazine-modified protein 112 (not illustrated by FIG. 4) and the second tetrazine-modified protein 117. In other examples, each of the first set of detection particles 124-A and/or the second set of detection particles 124-B is a latex (or other material) nanoparticle functionalized with at least one of the first tetrazine-modified protein 112 (not illustrated by FIG. 4) and the second tetrazine-modified protein 117. In some examples, the latex or other nanoparticles include a colored, fluorescent, magnetic, radioactive, or paramagnetic particle.

In various examples, use of the tetrazine-modified proteins bound to the particles as the detection particles may allow for controlled partial loading which enables more particles to bind to the test region 110. For example, the second set of detection particles 124-B may be bound to a volume of the tetrazine-modified protein 117 that is lower than a maximum volume that may be loaded on the particles, which may increase the lower detection limit for the RDT device 401. Said differently, the controlled partial loading may result in less than 100 percent loading of the second (or third) tetrazine-modified protein 117 (or other label protein) on the particle 129-B. The controlled partial loading may reduce the likelihood of multiple target analytes binding to the same detection particle, and conversely, increase the likelihood that multiple target analytes bind to different detection particles and increasing the detection signal. In response, a greater number of detection particles may be bound to a limited number of available target analytes in the biological sample, which are subsequently captured on the test region 110 to enhance the signal for (low) concentrations of the target analyte.

In some examples, a silane coupling agent may be used to functionalize GMF substrates and yield functionalized GMF substrates with functional groups (e.g., reactive moieties) such as, epoxide, carboxylic acid, anhydride, amine, etc. For membranes of other materials, other functionalization processes may be used. For example, grafting of glycidyl methacrylate to nitrocellulose membrane through electron beam irradiation may be used. These functional groups or reactive moieties on the substrate may be used further to modify the surface of the substrate in selected areas to provide a linker to a protein that contains unique moieties for orthogonal covalent bonding, to react/interact with a blocking agent for the remaining area to prevent non-specific binding, and to react with another compound to affect the flow rate of fluid. The reactive moieties on the linker, the blocking agent, and/or the other compound may be those that react or interact with the functional groups of the coupling agent on the substrate.

Accordingly, the linker used may be dependent on the functional groups on the functionalized substrate 102. For example, a TCO with an amino moiety used as a linker, a substrate that contains an epoxide, a carboxylic acid (or its derivative using 1-Ethyl-3-(3-(dimethylamino)propyl)carbodiimide (EDC)/N-hydroxysulfosuccinimide (sNHS)), or an anhydride may be used (e.g., may react with). Conversely, if the reactive moiety on the functionalized substrate is an amine, a carboxylic or an anhydride or an epoxide moiety may be used in the TCO. The selection of the linker may be dependent on the non-canonical amino acid incorporated into the tetrazine-modified protein. For example, a TCO or a norbornene may be used as linkers for a tetrazine-modified protein. Conversely, if TCO is incorporated into the protein as a part of the non-canonical amino acid, tetrazine may be the linker to link the protein to the substrate. Another example of the linker-non-canonical amino acid pairing is azide and alkyne, where one may serve as a linker to the other that is incorporated into a protein in the form of the non-canonical amino acid. As used herein, a noncanonical amino acid refers to or includes an amino acid that is not naturally-occurring, and therefore not among the list of 20 naturally-occurring amino acids. A non-limiting example of a noncanonical amino acid includes an amino acid that has been genetically encoded to include a tetrazine moiety at a predetermined amino acid site.

Various examples are directed to use of blocking agents and/or physical barrier to impact the flow rate. Using the same substrate for different functions in an RDT may make it difficult to the control of flow rate.

Various examples are directed to a single substrate that functions similarly to a traditional RDT, but without the use of multiple substrate which are assembled together. Each RDT, e.g., reagents forming the RDT, may be dispensed directly onto the single substrate with the appropriate surface modifications. An alternative to the RDT being dispensed onto the substrate, components may be combined with the sample at the time of testing and are wicked up the substrate for a test result, such as with a dipstick flow test and/or other tests.

FIGS. 5A-5H are schematic illustrations of example regions of an RDT device and detection particles. The various regions and/or components illustrated by FIGS. 5A-5H may be implemented in the apparatus 100 and/or device 101 of FIG. 1, the device 201 of FIG. 2, the kit 300 of FIG. 3, and/or apparatus 400 and/or device 401 of FIG. 4.

Figure 5A:
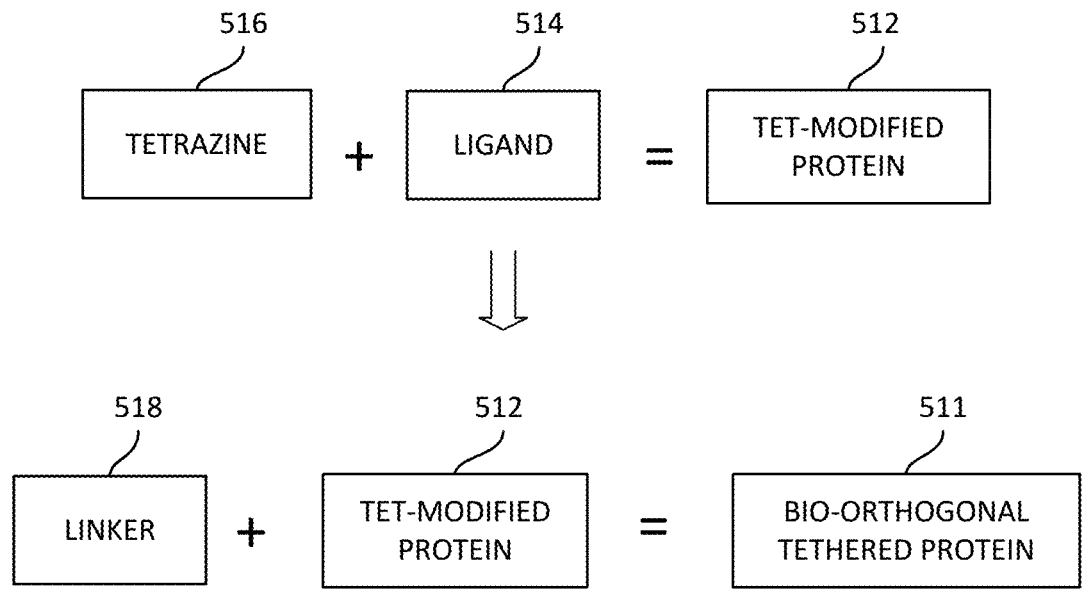
FIGS. 5A-5H are schematic illustrations of example regions of an RDT device and detection particles.

FIG. 5A is a block diagram schematically illustrating an example of forming a bioorthogonal tethered protein 511. The bioorthogonal tethered protein 511 may be used to form the capture agents and/or control agents, as described by FIG. 4. As further described herein, in some examples, the detection particles may include a bioorthogonal tethered protein.

The bioorthogonal tethered protein 511 may be formed on a substrate by attaching a tetrazine-modified protein 512 to a linker 518. The bioorthogonal tethered protein 511 may include a ligand 514 configured to bind to a target analyte and tetrazine 516. A concentration, a length, and an orientation of the bioorthogonal tethered protein may be configurable on the substrate. In various examples, the substrate may be configurable in the types, and amounts, of analytes that may be detected (e.g., bound) to the surface. For instance, the substrate may be configured to detect and/or bind to a particular target analyte in a sample (such as the SARS-CoV2 virus).

Protein translation uses tRNAs, which are aminoacylated by aminoacyl-tRNA synthetase enzymes, to read triplet codons in messenger mRNA) via base pairing interactions between the mRNA codon and the anticodon of the tRNA. In the example illustrated in FIG. 5A, a noncanonical amino acid such as a tetrazine 516 or tetrazine moiety may be site-specifically incorporated with a ligand 514 to form a tetrazine-modified protein 512 by attaching the tetrazine 516 or tetrazine moiety to a selector codon (e.g., STOP codon) of a gene. The resultant combination of the tetrazine 516 or tetrazine moiety with the ligand 514 is a tetrazine-modified protein 512.

For more general information on proteins attached to tetrazine, and specific information on example tetrazine structures, reference is made to US Patent Publication 2019/0077776, published on Mar. 14, 2019, and entitled "Reagents and methods for bioorthogonal labeling of biomolecules in living cells", which is herein incorporated by reference in entirety for its teachings.

The tetrazine-modified protein 512 may be prepared by genetic encoding using a non-canonical amino acid bearing a tetrazine moiety. For instance, referring to FIG. 5A, the tetrazine-modified protein 512 may be genetically encoded to include a ligand 514. Using an orthogonal aminoacyl-tRNA synthetase and an orthogonal tRNA, the noncanonical amino acid (in this case, a tetrazine or tetrazine moiety), a tetrazine-modified protein or tetrazine-modified functional protein fragment may be prepared that includes both the tetrazine 516 (or tetrazine moiety) and the ligand 514. In various examples, the ligand 514 includes a fragment or portion of a protein. For instance, a fragment of protein A may comprise the ligand 514, and the fragment of protein A may be genetically encoded to include the tetrazine 516 or tetrazine moiety to generate the tetrazine-modified protein 512.

Figure 5B:
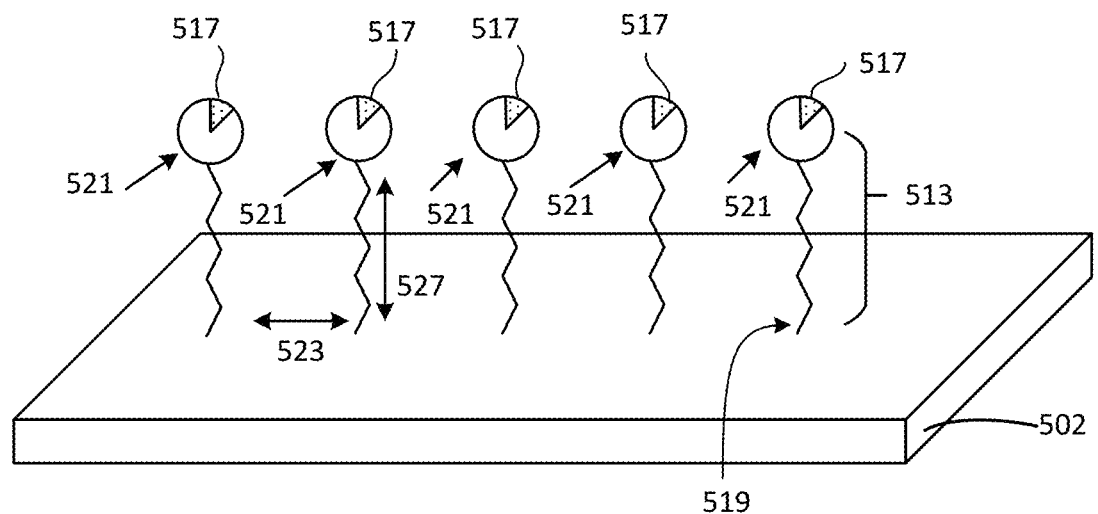

FIG. 5B is a schematic illustration of an example region of substrate. The region of the substrate may include a test region and/or a control region of the RDT device. As described with regards to FIG. 4, various RDT apparatuses and/or devices include a bioorthogonal tethered protein 513 which is deposited on a substrate 502 by attaching a tetrazine-modified protein to a linker 519. The tetrazine-modified protein may be formed by contacting a tetrazine molecule with a ligand (e.g., 521). The combination of the linker and tetrazine-modified protein may provide for ordered deposition of the ligand. For example, the ordered deposition may result in each ligand being positioned with the analyte binding site in a particular orientation. In some examples, the analyte binding site of each ligand may be facing or standing up. Through the controlled orientation, each binding site of the bound protein may be oriented in the same way, which may provide for optimization of the binding affinity (e.g., Kd) and which may prevent or mitigate non-specific binding and/or provide a 100-1000 fold improvement in detection indicator signal.

In some examples, the linker 519 is deposited on the substrate 502, and the tetrazine-modified protein is then deposited on the substrate 502. In other examples, the bioorthogonal tethered proteins 513 are formed and then deposited.

As illustrated in FIG. 5B, a plurality of bioorthogonal tethered proteins 513 may be tethered to the substrate 502. Each bioorthogonal tethered protein 513 includes a ligand 521 capable of binding an analyte 517, and a linker 519. In some examples, the length, concentration, and orientation of the bioorthogonal tethered protein 513 are selected based on the target analyte to be detected. For instance, the plurality of bioorthogonal tethered proteins 513 may be formed on the substrate 502 in such a manner that the orientation of a binding domain of each of the ligands 521 is facing in a same direction (as illustrated). Similarly, the plurality of bioorthogonal tethered proteins 513 may be formed on the substrate 502 in a manner such that the concentration 523 of the bioorthogonal tethered proteins 513 on the substrate 502 allow for each of the bioorthogonal tethered proteins 513 to bind to a target analyte 517. Yet further, the plurality of bioorthogonal tethered proteins 513 may be formed on the substrate 502 in a manner such that the length 527 of the bioorthogonal tethered proteins 513 on the substrate 502 allow for each of the bioorthogonal tethered proteins 513 to bind to a target analyte 517.

In some examples, the bioorthogonal tethered protein 513 are selectively formed on the substrate 502. Forming the bioorthogonal tethered protein 513 may include depositing a coupling agent to at least a portion of the substrate 502 and contacting the linker 519 with the coupling agent. As a specific example, a silane coupling agent may be deposited on the substrate 502 and the substrate 502 may be treated with TCO, resulting in the TCO binding to the silane coupling agent.

Figure 5C:
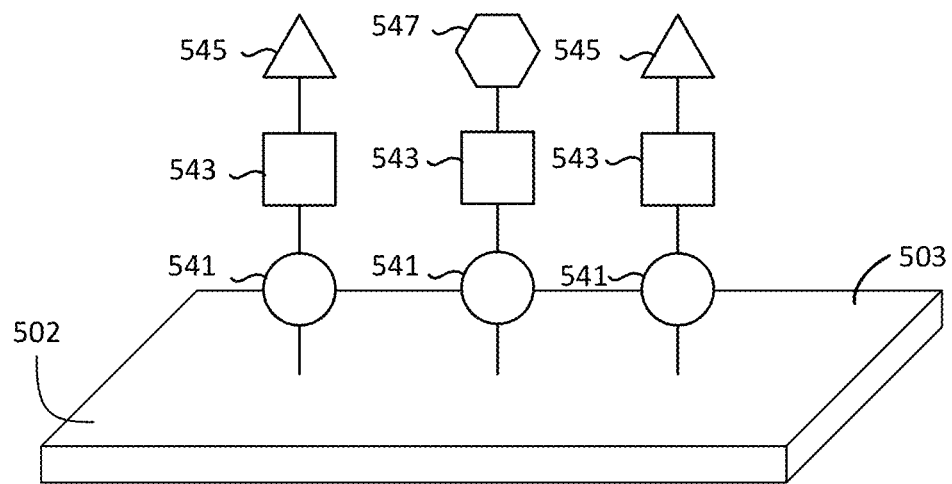
Figure 5D:
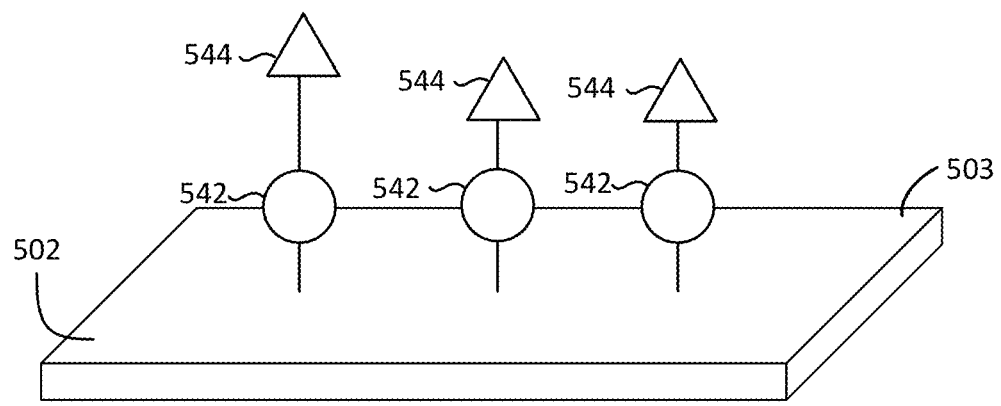

FIGS. 5C-5D are schematic illustrations of example regions of another RDT device, such as the RDT device 201 of FIG. 2. As previously described, a linker may or may not be present in or coupled to the capture agents and/or the control agents of the RDT device, depending on what functional group on the protein is immobilized to the substrate 502. In some examples, the first ligands of the (first subset of) capture agents and/or the analyte protein of the control agents are capable of binding to the functional group of the coupling agent 503 and are bound directly to the coupling agent 503 (not illustrated by FIGS. 5C-5D). In other examples, as shown by FIGS. 5C-5D, each of (the first subset of) the set of capture agents include a first linker bound to the coupling agent 503 in the first portion of the substrate, wherein the first ligand is bound to the first linker (and the test region further includes a first set of detection particles, not illustrated by FIGS. 5C-5D for ease of reference). In some examples, as shown by FIGS. 5C-5D, each of the set of control agents include a second linker bound to the coupling agent 503 in the third portion of the substrate 502, wherein the analyte protein is bound to the second linker.

Although not illustrated, in some examples, each of the first and second set of detection particles, such as the first and second set of detection particles 124-A, 124-B in FIG. 4, may further include a third and/or fourth linker bound to the particles and bound to the label protein or the second subset of set of capture agents. As previously described, the first, second, third, and/or fourth linkers may include the same type or different types of linkers.

FIG. 5C is a schematic illustration of an example substrate with a tetrazine-poly(ethylene glycol) (tet-PEG) polymer, where the tet-PEG polymer is used as a blocking agent. Similar to FIG. 5B, the region of the substrate 502 may include a test region and/or control region, and the substrate 502 includes a plurality of bioorthogonal tethered proteins. The tet-PEG may prevent non-specific binding to particular aspects of the substrate 502, in effect reducing signal noise. For example, the region of the substrate 502 illustrated in FIG. 5C includes three tethered molecules. Each of the tethered molecules include a linker 541 tethered to the coupling agent 503 of the substrate 502, and a tetrazine or tetrazine fragment 543 tethered to the linker 541. In some examples, as illustrated by FIG. 5C, tet-PEG and tetrazine-modified protein are in parallel, both tethered to the substrate 502 via the linker 541. A PEG molecule 545 is tethered to a tetrazine or tetrazine fragment 543. The third bioorthogonal tethered protein illustrated in FIG. 5C includes a ligand 547 tethered to a tetrazine or tetrazine fragment 543. The PEG molecule 545 may optionally be attached to remaining linkers 541 that are not attached to the tetrazine-modified protein, e.g., 543 and 547, and which may mitigate or prevent non-specific binding of the target analyte. The PEG polymer may provide a wider dynamic range and allow for keeping the sample undiluted, such that quantitative results may be obtained.

Example are not limited to using PEG as a blocking agent. For instance, an ethanolamine may be used to block amine reactive sites. Other example blocking agents include compounds that include amino moieties that may be used to block amine reactive sites introduced in the substrate functionalization process, such as 1-butylamine. Conversely, if the reactive moiety/functional group introduced in the functionalization process is carboxylic acid or anhydride reactive, the blocking agents may contain carboxylic acid or anhydride. If the linker is less prone to non-specific binding, the blocking agent application step for the linker may not be included (e.g., the substrate or a portion thereof may not include a blocking agent or an additional blocking agent).

As used herein, designations of "first", "second", "third", "fourth" are used to refer to one element and another of the same element, of the same type or of a different type, without reference to temporal order. As such, a first portion of the linker may be tethered to a ligand whereas a second portion of the linker may be tethered to PEG or another blocking agent, without reference to a temporal order of deposition. In some examples, the order of deposition of ligand and PEG may be specified.

For instance, and as a specific non-limiting example, the reagents may be loaded on the RDT device by first treating the surface of the substrate 502 with NaOH, followed by trimethoxysilane and which results in trimethoxysilane bound on the surface. The surface is then treated with TCO-NH2, resulting in TCO bound to silane. For example, once the trimethoxysilane is reacted, trimethoxy groups may no longer be present. The surface is then treated with the tetrazine-modified protein and the tet-PEG polymer (if relevant), resulting in the tetrazine-modified protein being tethered to a portion of the volume of TCO and tet-PEG polymer being bound to the remaining portion of the volume of TCO (if relevant).

Accordingly, in some examples, forming the bioorthogonal tethered protein includes depositing a volume of the linker 541 to the substrate 502 in a test region of the RDT device, and optionally in a control region of the RDT device. The method may further include attaching the tetrazine-modified protein, e.g., 543 and 547 illustrated in FIG. 5C, to at least a first portion of the linker 541. The method may optionally include attaching a tet-PEG polymer to a second portion of the linker 541.

In some examples, the bioorthogonal tethered protein includes the tetrazine-modified protein or tetrazine-modified functional protein fragment in a configured orientation. As used herein, "bioorthogonal" may include or refer to the amino acid tether embedded in the protein structure having no (or minimal) effect on the folding or activity of the ligand.

As described above, in some examples, the control agents of the control region may include a tetrazine-modified protein, and may include at least some of the same features and attributes as described by FIGS. 5B-5C. For example, in some examples, each of the set of control agents includes a (third) bioorthogonal tethered protein and the analyte protein includes a (third) tetrazine-modified protein (which forms part of the third bioorthogonal tethered protein). As previously described, the control region is used to verify that the reagents function properly in the absence of the analyte. In the case of detecting IgG, on the test region, various chemistries may be used to immobilize anti-IgG on the membrane and tested with the protein binding assay. Similarly, on the control region, various chemistries may be used to immobilize an IgG used to bind to an anti-IgG forming part of the detection particles.

However, examples are not so limited and either or both of the control region and the test region may not include tetrazine-modified proteins. For example, the control agents may include other types of ligands that bind to the substrate (directly or indirectly through a linker) that includes other types of proteins. Similarly, the capture agents may include other types of ligands that bind to the substrate (directly or indirectly through a linker) and are specific for a particular antigen.

FIG. 5D is a schematic illustration of an example region of the substrate 502, which may include a test region and/or control region, and the substrate 502 includes a plurality of proteins. As previously described, examples are not limited to tet-modified proteins. In some examples, each of the (first subset of the) set of capture agents of the test region and/or control agents of the control region may include a first ligand or analyte protein 544 and a linker 542. The linker 542 may be bound to the first ligand or analyte protein 544 and to the respective portion of the substrate 502 (e.g., to the coupling agent 503). As previously described, a linker may be used when the first ligand or analyte protein 544 is unable to bind to the functional group of the coupling agent and/or binds at a rate below a threshold. In some examples, the first ligand or analyte protein 544 may not readily bind in a proper orientation while retaining a threshold (e.g., sufficient to bind to its target) avidity due to the size of the protein. As the first ligand or analyte protein 544 decreases in size there are less opportunities to randomly orient the first ligand or analyte protein 544 in a way the first ligand or analyte protein 544 is able to capture or bind to a detection particle.

Figure 5E:
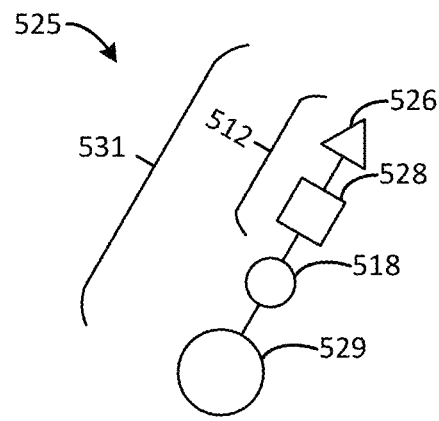

FIG. 5E is a schematic illustration of an example detection particle 525 that includes at least one bioorthogonal tethered protein 531 including a tetrazine-modified protein 512 bound to a surface of the particle 529 that exhibits a detectable label (e.g., colorant or other detectable signal). The tetrazine-modified protein 512 includes a tetrazine 528 bound to a ligand 526 configured to bind to at least one target. The ligand 526 may include the first ligand 114 or second ligand 126 illustrated by FIG. 1. That is, the detection particle 525 may form part of the first or second sets of detection particles. In some examples, the ligand 526 is configured to bind to both of the target analyte and the control agent in the control region. In other examples, the ligand 526 is configured to bind to the target analyte only. As described above, the particle 529 may be an AuNP, a latex, or other nanoparticle that is functionalized with the at least one tetrazine-modified protein 512, although examples are not so limited. The detection particle 525 may contain more tetrazine-modified protein 512 than illustrated. In some examples, the detection particle 525 and/or each detection particle of the set includes a (second or fourth) linker 518. The linker 518 may be bound to the tetrazine-modified protein 512 and to the particle 529.

The detection particles may include variations. The detection particles 525 illustrated by FIGS. 5E-H may form part of the first set of detection particles or second sets of detection particles, and thereby include a label protein or a capture agent in some examples.

Figure 5F:
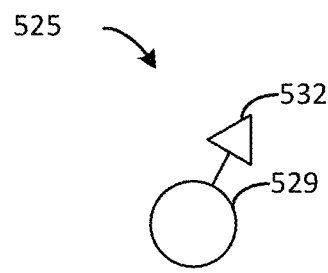

FIG. 5F is a schematic illustration of an example detection particle 525 that includes at least one label protein or capture agent 532 bound to a surface of the particle 529 that exhibits a detectable label. The label protein or capture agent 532 includes or is a ligand configured to bind to at least one target (e.g., the target analyte and/or the control agents). The label protein or capture agent 532 may be bound directly to the particle 529.

Figure 5G:
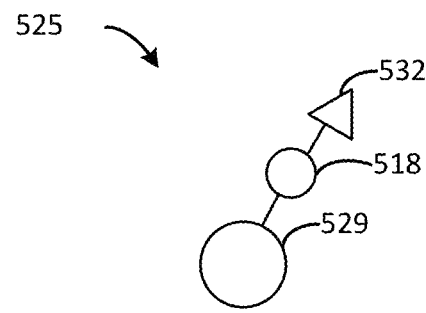

FIG. 5G is schematic illustration of an example detection particle 525 that includes at least one label protein or capture agent 532 bound indirectly to a surface of the particle 529 that exhibits a detectable label via a linker 518. As shown, the linker 518 is bound to the label protein or capture agent 532 and to the particle 529.

Figure 5H:
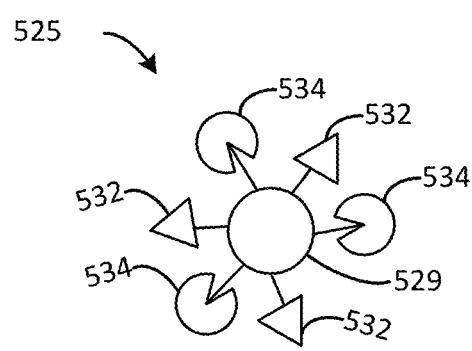

In some examples, at least some of the detection particles may include a blocking agent. FIG. 5H illustrates an example detection particle 525 that includes at least label protein or capture agent 532 bound (directly or indirectly via a linker (not shown)) to a surface of the particle 529 that exhibits a detectable label and at least one blocking agent 534. Although not shown, the label protein or capture agent 532 may include a tetrazine-modified protein, in some examples, and/or may be bound to the particle 529 via a linker, thereby forming bioorthogonal tethered proteins. Further, although the label protein or capture agent 532 and the blocking agent 534 are illustrated in equal volume (e.g., three each), examples are not so limited and may include more or fewer of the label protein or capture agent 532 and the blocking agent 534 than illustrated.

Figure 6:
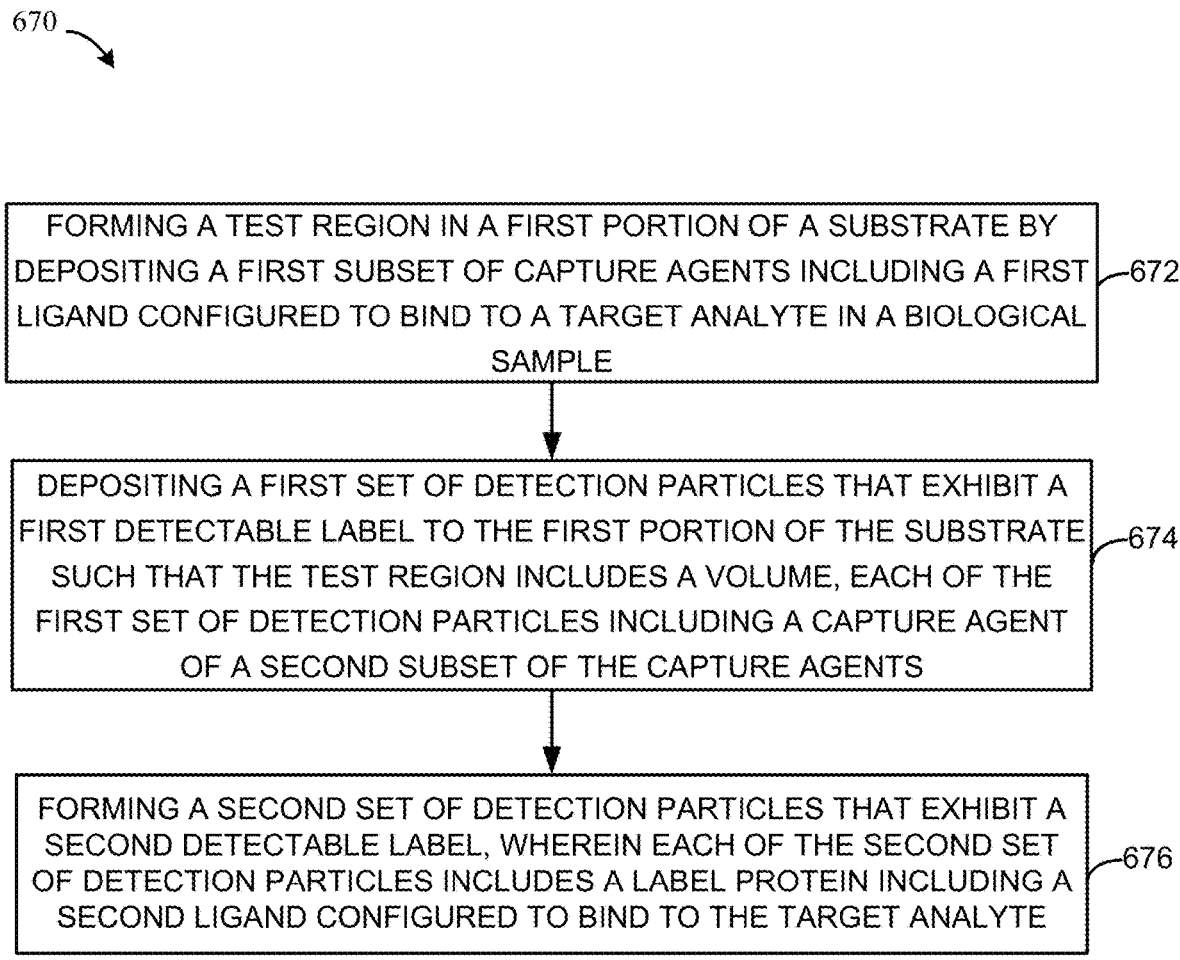
FIG. 6 is a block diagram schematically illustrating an example method of forming an RDT apparatus.

FIG. 6 is a block diagram schematically illustrating an example method of forming an RDT apparatus. In some examples, the reagents (e.g., coupling agent, capture agents, control agents, and, optionally detection particles and linkers) may be deposited on the substrate digitally via printing or analog technique. Digital printing may dial in the amount of typically expensive reagents and reduce waste. In addition, digital printing provides additional controls over analog dispensing. The placement of the drops may be optimized in the X-Y plane. The penetration of the reagent into the substrate may be optimized through the selection of drop volume, number of drops placed at a given site (number of passes) for a given total volume. These optimizations may directly or indirectly lead to enhanced signals. A single functionalized substrate makes printing down various reagents more convenient and economical. However, examples are not so limited and may include other techniques for forming a substrate and/or may not include a functionalized substrate.

As shown at 672, the method 670 includes forming a test region in a first portion of a substrate by depositing a first subset of capture agents including a first ligand configured to bind to a target analyte in a biological sample. The first subset of captures may include all of the capture agents or a subset of the total capture agents, in different examples. As shown at 674, the method 670 includes depositing a first set of detection particles that exhibit a first detectable label to the first portion of the substrate such that the test region includes a volume. In some examples, each of the first set of detection particles include a capture agent of a second subset of the capture agents, although examples are not so limited. And, at 676, the method 670 includes forming a second set of detection particles that exhibit a second detectable label, wherein each of the second set of detection particles includes a label protein including a second ligand configured to bind to the target analyte. Forming the second set of detection particles may include binding the label protein to a surface of particles to form the second set of detection particles.

In some examples, depositing the first set of detection particles comprises depositing a concentration of the first detectable label to provide a signal below a detection threshold associated with the first detectable label such that the first detectable label is preloaded on the test region to a level below a detection limit of the first detectable label. As previously described, the first set of detection particles may lower the LOD as compared to an RDT device without preloaded detection particles in the test region.

In some examples, the method 670 may further include determining the concentration of the first detectable label to preload onto the test region. For example, different concentrations of the first detectable label may be prepared and deposited onto different RDT devices in the respective test regions. The resulting test regions may be blocked and washed, and then scanned to determine the color intensity verses the concentration of the first detectable label, and the concentration may be extrapolated to the intensity of zero to determine a baseline for preloading concentration. The determined concentration is related to or based on the baseline for preloading concentration. In some examples, the determined concentration may be the same as the baseline for preloading concentration or may be a percentage less or more, which may be dependent on the detection methodology.

In some examples, each of the first set of detection particles include a capture agent of a second subset of the capture agent, and the method 670 further includes preparing the first set of detection particles by binding the second subset of the capture agents to a surface of the first set of detection particles. The prepared first set of detection particles may then be deposited to the first portion of the RDT device forming the test region.

In some examples, the method 670 includes forming at least a portion of a sample input region in a second portion of a substrate by depositing the second set of detection particles in the second portion. In other examples and/or in addition, the method 670 includes dispersing the second set of detection particles in solution. The solution may be mixed with a biological sample by a user and the sample input region may be placed in the solution.

In some examples, the method 670 further includes forming a control region in a third portion of a substrate by depositing a set of control agents including an analyte protein. In some examples, the control agents may be formed, as described above.

In some examples, the method 670 further includes depositing at least one blocking agent to at least one of: (i) the test region, (ii) the first set of detection particles) and (iii) the second set of detection particles. In some examples, the method 670 further or alternatively includes depositing the at least one blocking agent to the (iv) the control region, and/or (v) the sample input region. For example, in some examples, the at least one blocking agent may be applied to the particles as a quenching step and to the test region for the capture agents. The at least one blocking agent may include the same agent or different agents.

In various examples, at least one of the depositions of the method 670 includes digitally dispensing the reagents using inkjet printing (e.g., piezo, thermal, or continuous inkjet (CIJ)) or other inkjet printing technologies. Examples are not so limited and may include other dispensing techniques.

In various examples, an RDT device may be formed, which includes the substrate described herein. For instance, an RDT device (also referred to herein as an "assay device") may start with a liquid sample (or its extract) containing a target analyte. The liquid sample may move without the assistance of external forces (capillary action) through various zones on which molecules may interact with the RDT device. Non-limiting examples of an RDT device may include a test strip, a microfluidic device with microfluidic channels, and other assay devices. Example assays include LFA, chemiluminescent immunoassays, among other plate assays or other types of assay tests, such as isotopic immunoassay, fluoroimmunoassay, radioimmunoassay, microbiologic assays, quantal or graded bioassays, and others. The sample may be applied at one end of the RDT device, and the sample may migrate through the various zones in the RDT device, and recognition of the analyte results in a response on the test region, while a response on a control region indicates the proper liquid flow through the RDT device. The sample may also be introduced to the test region without going through various zones by being directed immediately to a test region. The read-out, which may indicate a qualitative or quantitative assessment of the analyte, may be assessed by eye or using a dedicated reader. In order to test multiple analytes simultaneously under the same conditions, additional test regions of ligands specific to different analytes may be immobilized in an array format. In some examples, multiple test regions or sub-regions of a test region may be loaded with the same ligand and different concentrations of the first set of detection particles on the test regions or sub-regions of the test region and may be used for quantitative or semi-quantitative assays.

In some examples, the tetrazine-modified protein is attached to the linker in a configured orientation to permit binding of the target analyte. The bioorthogonal tethered protein may include a configured length of the tetrazine-modified protein comprising a chain of a plurality of binding domains to the analyte. For instance, a ligand may be repeated a number of times, such as three times, resulting in a chain of binding domains for the target analyte.

For more general information on proteins attached to tetrazine (Tet), and specific information on techniques to immobilize tetrazine on porous membranes, reference is made to: US Patent Publication 2021/0072238, published on Mar. 11, 2021, and entitled "Immobilization of proteins with controlled orientation and load", which is herein incorporated by reference in its entirety for its teachings; and to WO 2022/109075 (PCT/US2021/059798), published on May 27, 2022, and entitled "Configurable Substrate of a Fluidic Device", which is herein incorporated by reference in its entirety for its teachings. For more specific and general information on the preparation of representative tetrazine non-canonical amino acids, methods for genetic encoding proteins and polypeptides using the tetrazine non-canonical amino acids, and proteins and polypeptides comprising the tetrazine non-canonical amino acids reference is made to WO 2016/176689 (PCT/US2016/030469), published on Nov. 3, 2016, and entitled "Reagents and methods for bioorthogonal labeling of biomolecules in living cells", which is herein incorporated by reference in its entirety for its teachings.

Generally, manufacturing an RDT device includes a plurality of steps that may be performed in various orders. In some examples, the methods of manufacturing include creating a region, where reagents are to be dispensed onto the substrate.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

Experimental/More Detailed Embodiments

As further illustrated below in connection with experimental examples, a substrate for an RDT was modeled and tested, evidencing the capability to form an RDT device with preloaded detection particles capable of detecting a particular target analyte, sensitive enough to detect small volumes of the target analyte, and scalable for mass-production and use in a point-of-care setting.

In various experiments, different target analytes where detected using test regions of RDT devices. The target analytes were in buffer fluid or otherwise in fluid associated a biological sample, such as saliva or blood. In some experiments, the target analyte was a spike glycoprotein of SARs-CoV-2. In other experiments, the target analyte was immunoglobulin G (IgG).

Figure 7B:
FIG. 7A-7B illustrate example experimental results for detecting a spike glycoprotein of severe acute respiratory syndrome coronavirus 2.
Figure 7A:
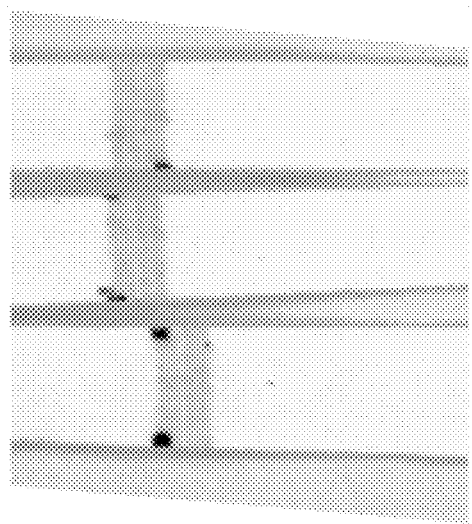

FIGS. 7A-7B illustrate example experimental results for detecting a spike glycoprotein of SARs-CoV-2. The spike glycoprotein of SARs-CoV-2 was used as the target analyte and detected on a test region of an RDT device using detection particles including a ligand of a tetrazine containing a nanobody (NBx) (e.g., a detectable label). Another tetrazine containing a nanobody (NBy) was printed on the test region and used as capture agents. FIG. 7A illustrates the resulting test region as tested with the spike glycoprotein of SARs-CoV-2 contained in a buffer solution and FIG. 7B illustrates the resulting test region as tested with the spike glycoprotein of SARs-CoV-2 in saliva. As shown by FIGS. 7A-7B, both the target analyte in buffer solution and in a biological sample of saliva were detected and resulted in a human visual signal (e.g., colored line) in the test regions. In the experimental examples, the substrate was functionalized with amine reactive moieties and a linker of TCO-NH2 was printed on the substrate. The spike glycoprotein of SARs-CoV-2 was from Thermo Fisher Scientific and included SARS-CoV-2 Spike Protein S1 (aa11-682), hFc-His Tag Recombinant Protein, Catalog #RP-87679. For more general and specific information on spike glycoprotein, reference is made to https://www.thermofisher.com/antibody/product/SARS-CoV-2-Spike-Protein-S1-aa11-682-hFc-His-Tag-Recombinant-Protein/RP-876791, which is incorporated herein by reference in its entirety for its teaching.

Various experiments were preformed to assess preloading concentration of the detectable label. To assess the preloading concentration, a series of concentrations of AuNP-capture agent were prepared based on a starting point LOD as described in Khlebtsov, et al., "Quantifying the Number of Gold Nanoparticles in the Test Zone of Lateral Flow Immunoassay Strips", ACS Appl. Nano Mater., 2019, 2, 5020-5028, referred to generally as "KLOD" for ease of reference, and were printed on a test region, blocked and optionally washed. The resulting test regions were scanned and color intensity measured. The color intensity was plotted against the AuNP-capture protein concentrations in factors of the KLOD. Extrapolation of the regression of the curve led to the zero intensity concentration.

Figure 8:
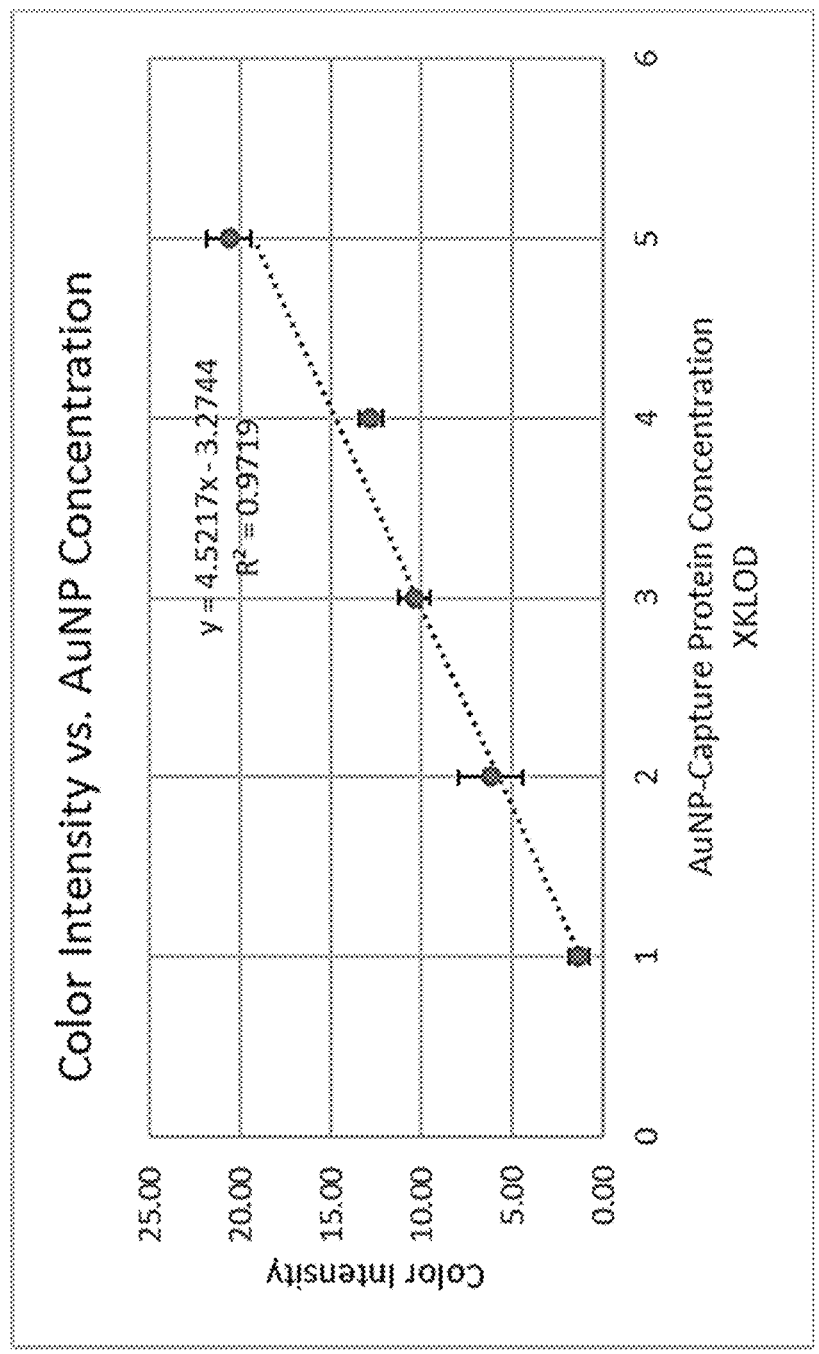
FIG. 8 illustrates example experimental results for determining a preloading concentrations for an RDT device.

FIG. 8 illustrates example experimental results for determining a preloading concentration of a detection label for an RDT device. In this experiment, this value is about 0.7× KLOD. This may serve as the baseline for the preloading concentration, with a plurality of concentrations of the detection label tested being below the baseline. The XKLOD (e.g., 0.7×KLOD) is the number of AuNP per $mm^2$ to reach the detection threshold for a machine scan. For a visual threshold, e.g., visible by the human eye, further tuning is performed. KLOD used is associated with or includes the limit of detection for the number of AuNP per $mm^2$ that is specific to test conditions including the type of particles, particle size, and substrate material as described by the above reference. The actual LOD and the baseline for the preloading concentration is different for specific test conditions. The baseline of 0.7×KLOD was used as the preloading concentration of the detection label (e.g., AuNP), which resulted in a concentration of signal provided by the detection label that was on the detection threshold of a machine scan (e.g., the scanned intensity is zero and not machine detectable) and not human visible.

Various experiments were directed to assessing preloading detection labels on a test region of an RDT device. In such experiments, the test region was formed by attaching a capture agent to a particle that exhibits a detectable label, such as forming AuNP-capture agent complexes. The preloading concentration was determined for the test region, as described in associated with FIG. 8. The detection particles were deposited onto the test region at the determined concentration and the capture agents were also deposited on the test region. Additionally, a blocking agent was applied to the test region.

Figure 9:
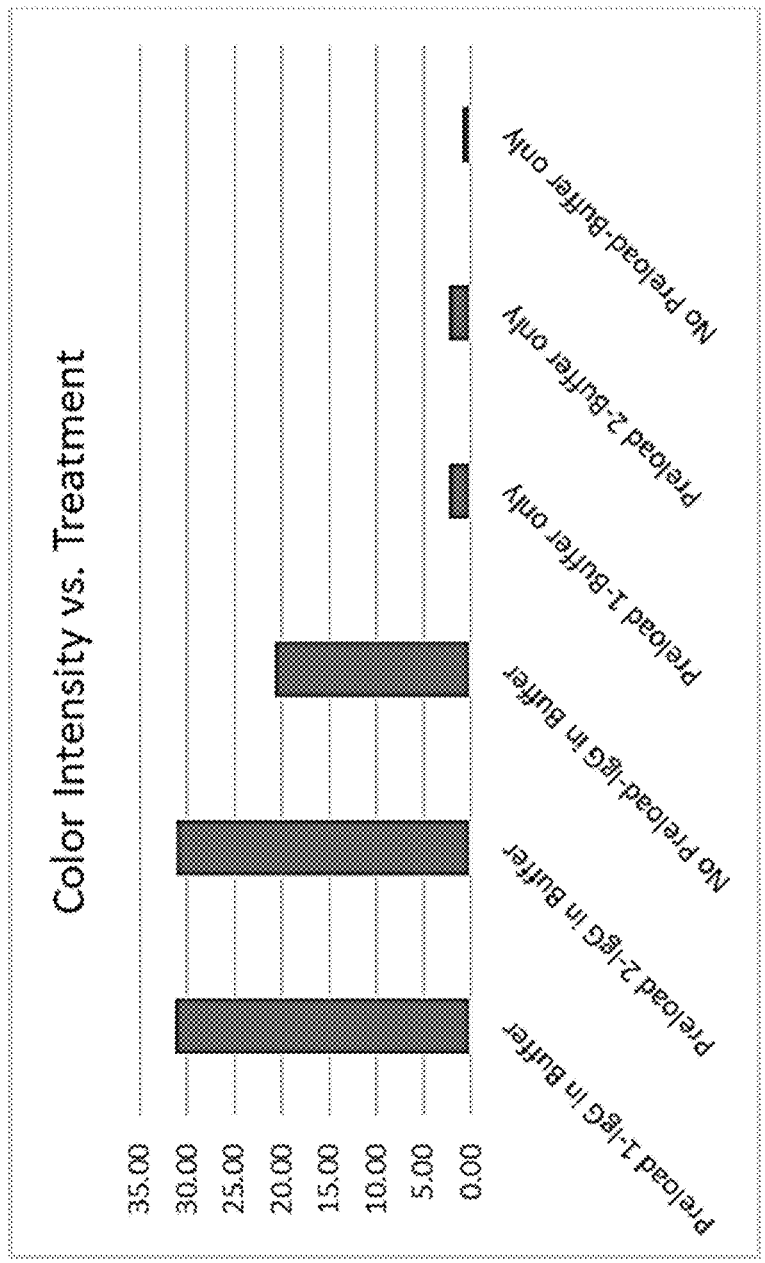
FIG. 9 illustrates example experimental results of preloading an RDT device with detection particles on the test region.

FIG. 9 illustrates example experimental results of pre-loading an RDT device with detection particles on the test region. In some experiments, the formed RDT device with preloaded detection particles on the test region were assessed by using fluid containing an IgG as the test analyte to demonstrate the effect of preloading detection particles on the test region. In an experiment, the detection particles included AuNP with a tetrazine-modified protein A3 bound thereto, herein generally referred to as "AuNP-tet-protein A3" for ease of reference. For running the test, protein A B1 was attached to AuNP to form the second set of detection particles (which are exposed to the test region), herein generally referred to as "AuNP-protein A B1" for ease of reference.

Three conditions were tested on the test region. The first condition, herein referred to as "Preload 1", has printed AuNP-tet-protein A3 on the test region, followed by a linker printed, and then tet-protein A3 printed as the capture agents which bind to the linker. The second condition, herein referred to as "Preload 2", printed AuNP-tet-protein A3 in a mixture with the linker, followed by tet-protein A3 printed on the test region. The third condition, used as a control and herein referred to as "No Preload", has the linker printed and then the tet-protein A3 printed on the test region. For each of the Preload 1, Preload 2, and No Preload, the IgG and AuNP-protein A B1 was applied. The test region, upon completion of the assay, was analyzed using colorimetric values to quantify the results in the form of color intensity.

More particularly, FIG. 9 is a graph illustrating the results of a machine scan of Preload 1, Preload 2, and No Preload as tested with IgG and AuNP-protein A B1 in buffer fluid applied or exposed to the test region (left side of the graph) and with no AuNP-protein A B1 (and no IgG) in buffer fluid applied to the test region (right side of the graph). The IgG was the same concentration in each buffer fluid. The buffer with no IgG may be used as a negative control with the No Preload being used as a positive control. As shown, the resulting color intensity was greater with Preload 1 and Preload 2, than with No Preload using the IgG and AuNP-protein A B1 in buffer fluid. The sequence of the preloading with regard to the AuNP and the linker (Preload 1 verses Preload 2) does not appear to effect the results. In the absence of IgG (Buffer only), the signal is close to zero. For example, the resulting color intensity of the Preload 1, Preload 2, and No Preload (left side of graph) were visible to the human eye (but with No Preload at lower intensity than Preload 1 and Preload 2), and the color intensity of the negative controls (right side of the graph) were not visible to the human eye.

In various examples, a digital dispensing device was used for reagent printing of at least some of the reagents and used in validating and manufacturing the RDT device. Solutions for a protein loading and partial loading protocol are included below in Tables 1 and 2.

TABLE 1

Reagents for Protein Loading Protocol

| Reagent | Viscosity at 25° C. (mPa-s) | Thermal Stability |
|---|---|---|
| Water | 0.89 | b.p. 100° C. |
| EtOH | 0.98 | b.p. 78.37° C. |
| 2M NaOH | >0.89 | b.p. 100° C. |
| Trimethoxysilane | ~0.56 | b.p. 110.6° C. |
| TCO amine | ~0.98 | Stable at 4° C. |
| Tween Buffer | >0.89 | c.p. 76° C. |
| Proteins or Protein Fragments | >0.89 | ~60° C. |
| Blocking Agent(s) | Various | various |
| Sucrose or Glucose | >0.89 | <100° C. |

TABLE 2

Reagents for Detection Particle Label Protein Loading

| Reagent | Viscosity at 25° C. (mPas) | Thermal Stability |
|---|---|---|
| TCO amine | ~0.98 | Stable at 4° C. |
| PO4 | 0.98 | b.p. 78.37° C. |
| NaCL | >0.89 | b.p. 100° C. |
| Protein or Protein Fragments | >0.89 | ~60° C. |
| Blocking Agent(s) (e.g., Quench Solution) | Unknown | unknown |
| Buffer | >0.89 | c.p. 76° C. |
| Sucrose or Glucose | >0.89 | <100° C. |

Note that the following are abbreviations: b.p is for boiling point, and c.p. is for cloud point.

In some examples, the reagents were loaded on the RDT device by treating the surface of the substrate with NaOH, followed by trimethoxysilane and which results in trimethoxysilane bound on the surface. The surface was then treated with TCO-NH2, resulting in TCO being bound to the silane. The substrate surface was then treated with the tetrazine-modified protein and the tet-PEG polymer (e.g., Tet-PEG-5K), resulting in the bioorthogonal tethered protein being tethered to a first portion of the volume of TCO and the tet-PEG polymer being bound to a second portion of the volume of TCO. The surface was then treated with another blocking agent. In some examples, the tet-PEG was not used. In various examples, casein was used as a blocking agent which was applied at least in the sample input region after the tet-protein was deposited and before the detection particles are deposited.

The invention claimed is:

1. A rapid detection test (RDT) apparatus, comprising:
    a substrate;
    a test region disposed on a first portion of the substrate, the test region including:
        a first set of detection particles that exhibit a first detectable label; and
        a set of capture agents configured to bind to a target analyte in a biological sample, each of the set of capture agents including a first ligand configured to bind to the target analyte; and
        a second set of detection particles that exhibit a second detectable label, wherein each of the second set of detection particles includes a label protein including a second ligand configured to bind to the target analyte.

2. The RDT apparatus of claim 1, wherein a first subset of the set of capture agents are bound to the substrate and a second subset of the set of capture agents form part of the first set of detection particles.

3. The RDT apparatus of claim 1, wherein the first set of detection particles include a concentration of the first detectable label that provides a signal below a detection threshold associated with the first detectable label, wherein the signal is human visible or machine detectable when above the detection threshold.

4. The RDT apparatus of claim 1, wherein the first ligand and the second ligand is configured to bind to a spike glycoprotein or other target of severe acute respiratory syndrome coronavirus 2 (SARs-CoV-2), and wherein the first set of detection labels that exhibit the first detectable label are preloaded in the test region to a level below a detection limit of the first detectable label prior to exposure of the test region to the biological sample.

5. The RDT apparatus of claim 1, wherein the first detectable label of the first set of detection particles is different from the second detectable label of the second set of detection particle, and the first detectable label and the second detectable label are additive to one another.

6. The RDT apparatus of claim 1, wherein the first detectable label of the first set of detection particles is the same as, and additive to, the second detectable label of the second set of detection particles.

7. The RDT apparatus of claim 1, wherein the first ligand and the second ligand are different from one another.

8. The RDT apparatus of claim 1, wherein:
the apparatus further includes a control region disposed on a third portion of the substrate, the control region including a set of control agents, each of the control agents including an analyte protein and where the label protein includes the second ligand configured to bind to both the target analyte and the analyte protein of the set of control agents.

9. The RDT apparatus of claim 1, further including at least one of:

a sample input region disposed on a second portion of the substrate, the sample input region including the second set of detection particles; and a sample container that includes a solution with the second set of detection particles, the sample container configured to receive the biological sample and to provide the biological sample and the second set of detection particles to a sample input region of the substrate.

10. The RDT apparatus of claim 1, wherein each of the first set and second set of detection particles are a gold nanoparticle (AuNP) or a latex nanoparticle respectively functionalized with one of the first ligand and the label protein.

11. A rapid detection test (RDT) device, comprising:
a substrate;
a test region disposed on a first portion of the substrate, the test region including:

a first set of detection particles that exhibit a first detectable label; and a set of capture agents configured to bind to a target analyte in a biological sample, each of the capture agents including a first ligand configured to bind to the target analyte; and a sample input region disposed on a second portion of the substrate, the sample input region including a second set of detection particles that exhibit a second detectable label, wherein each of the second set of detection particles includes a label protein including a second ligand configured to bind to the target analyte.

12. The device of claim 11, wherein the first set of detection particles include a concentration of the first detectable label that provides a signal below a detection threshold associated with the first detectable label and lowers a limit of detection of the RDT device, wherein the first set of detection particles that exhibit the first detectable label are preloaded in the test region and provide the signal below the detection threshold prior to exposure of the test region to the biological sample.

13. The device of claim 11, wherein the target analyte is associated with severe acute respiratory syndrome coronavirus 2 (SARs-CoV-2), and wherein a first subset of the set of capture agents are bound to the substrate and a second subset of the set of capture agents form part of the first set of detection particles.

14. The device of claim 11, the RDT device further including a control region disposed on a third portion of the substrate, the control region including a set of control agents, each of the control agents including an analyte protein and where the label protein includes the second ligand configured to bind to both the target analyte and the analyte protein of the set of control agents.

15. The device of claim 11, wherein:

each of the first set of detection particles is a gold nanoparticle (AuNP) or a latex nanoparticle; and each of the second set of detection particles is an AuNP or a latex nanoparticle functionalized with at least one of the label protein.

16. A method, comprising:

forming a test region in a first portion of a substrate by depositing a first subset of capture agents including a first ligand configured to bind to a target analyte in a biological sample;

depositing a first set of detection particles that exhibit a first detectable label to the first portion of the substrate such that the test region includes a volume; and forming a second set of detection particles that exhibit a second detectable label, wherein each of the second set of detection particles includes a label protein including a second ligand configured to bind to the target analyte.

17. The method of claim 16, wherein depositing the first set of detection particles includes depositing a concentration of the first detectable label that provide a signal below a detection threshold associated with the label protein such that the first detectable label is preloaded on the test region to a level below a detection limit of the first detectable label, wherein accumulation of the second detectable label in the test region is configured to add to the signal provided by the first detectable label, and once the detection threshold is reached, the signal is detectable.

18. The method of claim 17, further including determining the concentration of the first detectable label to preload onto the test region.

19. The method of claim 16, wherein each of the first set of detection particles further include a capture agent of a second subset of the capture agents, and the method further includes preparing the first set of detection particles by binding the second subset of the capture agents to a surface of the first set of detection particles.

20. The method of claim 16, further including depositing at least one blocking agent to at least one of:

the test region, the first set of detection particles, and the second set of detection particles.

* * * * *